US011524051B2

(12) United States Patent
Millenbaugh et al.

(10) Patent No.: US 11,524,051 B2
(45) Date of Patent: *Dec. 13, 2022

(54) METHODS OF TREATING FUNGAL INFECTIONS

(71) Applicant: United States of America as represented by the Secretary of the Navy, Silver Spring, MD (US)

(72) Inventors: Nancy Millenbaugh, San Antonio, TX (US); Jeremy Wesley Gleaton, Cleveland, OH (US); Dickson Kiprono Kirui, San Antonio, TX (US); Sabrina Snyder, San Antonio, TX (US); Crystal Rock, San Antonio, TX (US)

(73) Assignee: The United States of America as Represented by the Secretary of the Navy, Arlinton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/011,165

(22) Filed: Sep. 3, 2020

(65) Prior Publication Data

US 2020/0397862 A1  Dec. 24, 2020

Related U.S. Application Data

(60) Continuation-in-part of application No. 16/717,726, filed on Dec. 17, 2019, now Pat. No. 10,946,065, which is a division of application No. 15/906,863, filed on Feb. 27, 2018, now Pat. No. 10,548,948.

(60) Provisional application No. 62/466,195, filed on Mar. 2, 2017, provisional application No. 62/548,506, filed on Aug. 22, 2017.

(51) Int. Cl.
| | |
|---|---|
| *A61K 38/10* | (2006.01) |
| *A61K 38/17* | (2006.01) |
| *A61K 45/06* | (2006.01) |
| *A61P 31/00* | (2006.01) |
| *A61L 15/44* | (2006.01) |
| *A61L 15/46* | (2006.01) |

(52) U.S. Cl.
CPC .......... *A61K 38/1767* (2013.01); *A61K 45/06* (2013.01); *A61L 15/44* (2013.01); *A61L 15/46* (2013.01); *A61P 31/00* (2018.01); *A61L 2300/25* (2013.01); *A61L 2300/252* (2013.01); *A61L 2300/404* (2013.01)

(58) Field of Classification Search
CPC .... A61K 38/10; A61K 38/1767; A61K 45/06; A61K 38/17; A61P 31/00
See application file for complete search history.

(56) References Cited

U.S. PATENT DOCUMENTS

| | | | |
|---|---|---|---|
| 2007/0237809 A1 | 10/2007 | Phaneuf et al. | |
| 2009/0258045 A1* | 10/2009 | Chuang | A61L 27/54 424/409 |
| 2010/0047324 A1 | 2/2010 | Fritz et al. | |
| 2016/0151534 A1* | 6/2016 | Fleiszig | A61L 26/0047 514/2.3 |
| 2017/0044222 A1* | 2/2017 | Alexander | A61L 27/54 |

FOREIGN PATENT DOCUMENTS

WO  2016/161997 A1  10/2016

OTHER PUBLICATIONS

Andrea, A., et al., (2018) Biomolecules, 8, 27, 1-29.
Bacalum, M., et al., (2015) Int J Pept Res Ther, 21: 47-55.
Wu, X., et al., (2014) Antimicrobial Agents and Chemotherapy, 58: 5342-5349.
Chandra, J., et al., (2001) Journal of Bacteriology, 183: 5385-5394.
Bulet, P., et al., (1999) Developmental and Comparative Immunology, 23: 329-344.
Marr, A., et al., (2006) Current Opinion In Pharmacology, 6: 468-472.
Chen, W., et al., (2016) Future Science OA FSO348.
Matsuzaki, K., (2009) Biochemica et Biophysica Acta, 1788: 1687-1692.
Lin, H., et al., (2012) Biomatter, 2:4, 321-328.
Kulig, D., et al., (2016) Polymers, 8;167, 1-17.
Gomez Chabala., L. et al., (2017) Marine Drugs, 15;328, 1-13.
Szekalska, M., et al., (2017) Molecules, 22, 182, 1-20.
Paul, W., (2004) Trends in Biomaterials and Artificial Organs, 18: 18-23.
Qin, Y., (2008) Polymer International, 57: 171-180.
Piras, Anna., et al., (2015) Frontiers in Microbiology, 6: 1-10.
Babavalian, H., et al., (2015) Jundishapur J. Microbiol, 8(9); e28320.
Piras, A., et al., (2015) Pharm Res, 32: 2259-2265.
Liao, C., et al., (2005) Journal of Controlled Release, 104: 347-358.
Corzo, G., et al., (2001) Biochem J, 359: 35-45.
De la Fuente-Nunez, C., et al., (2015) Chem.Biol, 22: 196-205.
Macherla, C., et al., Front. Microbiol. 2012, 3:193.
Hamilton, J.R., et al., Infect. Immun., 1976, 14(4):982-9.
Zeng XC, et al., (2004) Peptides 25: 143-150.
Cao et al., (2012) PLoS ONE 7(7): e40135.
Heunis, T. D. J., & Dicks, L. M. T. BioMed Research International, (Journal of Biomedicine and Biotechnology) vol. 2010 (2010), Article ID 510682.
Heunis, T. D., et al. (2013) Antimicrobial Agents and Chemotherapy, 57(8), 3928-3935.
Heunis, T., et al. (2011) International Journal of Molecular Sciences, 12(4), 2158-2173.

(Continued)

*Primary Examiner* — Julie Ha
(74) *Attorney, Agent, or Firm* — NingYang

(57) ABSTRACT

Methods of treating a fungal infection in a subject in need thereof comprising administering to the subject a therapeutically effective amount of a composition comprising one or more antifungal peptides selected from the group consisting of BmKn2, dBmKn2, Kn2-7, and dKn2-7 are described. Antifungal pharmaceutical compositions and dosage forms, including field-deployable dosage forms, comprising one or more of these antifungal peptides are also described.

11 Claims, 15 Drawing Sheets

Specification includes a Sequence Listing.

(56) References Cited

OTHER PUBLICATIONS

Sebe, I., et al., (2016) Amino Acids, 48(1), 203-211.
Eriksen, T. H. B.,et al. (2013) Journal of Biomedical Nanotechnology, 9(3), 492-498.
Karlsson, et al. ACS Chemical Biology, vol. 4 No. 7, pp. 567-579 (2009).
Evans et al, J. Vis. Exp. (73),e50166, doi:10.3791/50166 (2013).
H. Jenssen, S.I. Aspmo, Serum stability of peptides, Peptide-Based Drug Design (2008) 177-186.
Mansour, S. C., et al. (2015) J. Pept. Sci., 21, 323-329.
Bessalle, R., et al., FEBS Letters, 1990, 274(1): p. 151-155.
Bink, A., Pellens, K., Cammue, B. P.A., and Thevissen, K., The Open Mycology Journal, 2011, 5:29-38.
Burrows, L.L., et al., J Antimicrob Chemother, 2006, 57(5): p. 899-907.
De la Salud Bea, R., M.R. Ascuitto, and L.E.L. de Johnson, Peptides, 2015. 68: p. 228-232.
De Lucca, A.J. and T.J. Walsh, Antimicrob Agents Chemother. 1999, 43(1): p. 1-11.
Gordon, Y.J., E.G. Romanowski, and A.M. McDermott, Current Eye Research, 2005. 30(7): p. 505-515.
Guilhelmelli, F., et al., Front Microbiol, 2016, 7:1844.
Heard, K.R., et al., Journal of Medicinal Chemistry, 2013. 56(21): p. 8339-8351.
Sengupta, J., et al., J Infect Chemother, 2012, 18(5): p. 698-703.
Lee, J. and Lee, D.G. FEMS Microbiology Letters, 2014. 355(1): p. 36-42.
Mandal, S.M., et al., Peptides, 2011. 32(8): p. 1741-1747.
Wang, K., et al., Peptides, 2014. 56: p. 22-29.
Weinstock, M.T., et al., Biopolymers, 2012. 98(5): p. 431-442.
Xu, T., et al., Infect Immun, 1991, 59(8): p. 2549-54.
Zhang, R., et al., Mol Immunol, 2010, 47(11-12): p. 2030-7.
Ifkovits, J. et al., (2009) JoVE 32 http://www.jove.com/index/Details.stp?ID=1589.
Ortiz, E. et al., Toxicon 93 (2015) 125-135.
Moerman, L. et al., European J. Biochem. 269 (2002) 4799-4810.
Harrison, P. et al. Toxicon 88 (2014) 115-137.
Zhao, Y. et al., AMB Expr (2016) 6:122 DOI 10.1186/s13568-016-0295-8.
Chen, Y. et al. PLoS One, (2012) 7(4):e34947.
Arpornsuwan, T. et al. Peptides (2014) 53:315-20.
De la Salud Bea, R. et al. Toxicon (2015) 101:79-84.
Satitmanwiwat, S. et al. Biomed Pharmacother. (2016) 84:1042-50.
Sanglard, D. and Odds, F.C., The Lancet Infect. Dis. (2002) 2(2):73-85.
International Search Report and Written Opinion dated May 17, 2018 for International Application PCT/US2018/019983.
Nikhitha et al., International Journal of Universal Pharmacy and Bio Sciences, Feb. 29, 2016, vol. 5, No. 1, pp. 81-92.
Ammons et al., Biofouling, Apr. 1, 2013, vol. 29, No. 4, pp. 443-455.
Elgar, et al. African Journal of Biotechnology, Dec. 29, 2006, vol. 5, No. 25, pp. 2495-2502.
Yeaman, M., et al., (2003) Pharmacological Reviews, 55: 27-55.
Zasloff, M. (2002) Nature, 415: 389-395.
Delattin, N., (2016) Curr Top Med Chem, 17: 604-612.
Van der Weerden et al., (2013) Cell Mol. Life Sci, 70: 3545-3570.
Brogden, K., (2005) Nature, 3: 238-250.
Gomes, A.P., et al., (2015) Carbohydrate Polymers, 127: 451-461.
Thaya, R., et al., (2018) Microbial Pathogenesis, 114: 17-24.
Yang, Y., et al., (2017) Regenerative Biomaterials, 299-307.

* cited by examiner

SEQUENCE LISTING

```
<160> NUMBER OF SEQ ID NOS: 3

<210> SEQ ID NO 1
<211> LENGTH: 13
<212> TYPE: PRT
<213> ORGANISM: Mesobuthus martensii Karsch

<400> SEQUENCE: 1

Phe Ile Gly Ala Ile Ala Arg Leu Leu Ser Lys Ile Phe
1               5                   10
```

```
<210> SEQ ID NO 2
<211> LENGTH: 13
<212> TYPE: PRT
<213> ORGANISM: Artificial Sequence
<220> FEATURE:
<223> OTHER INFORMATION: Experimental derivative of  Mesobuthus
      martensii Karsch peptide BmKn2

<400> SEQUENCE: 2

Phe Ile Lys Arg Ile Ala Arg Leu Leu Arg Lys Ile Phe
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Peptide 1018 is a synthetic peptide derived
      from bactenecin, a bovine neutrophil host defense peptide.

<400> SEQUENCE: 3

Val Arg Leu Ile Val Ala Val Arg Ile Trp Arg Arg
1               5                   10
```

METHODS OF TREATING FUNGAL INFECTIONS

CROSS REFERENCE TO RELATED APPLICATIONS

The present application is a Continuation-in-Part Application of U.S. Nonprovisional patent application Ser. No. 16/717,726 filed Dec. 17, 2019 which claims the benefit of U.S. Nonprovisional patent application Ser. No. 15/906,863 filed Feb. 27, 2018 and which issued Feb. 4, 2020 as U.S. Pat. No. 10,548,948, and which claims the benefit of U.S. Provisional Patent Application No. 62/466,195 filed Mar. 2, 2017, and the benefit of U.S. Provisional Patent Application No. 62/548,506 filed Aug. 22, 2017, the entire disclosures of which are incorporated by reference herein.

SEQUENCE LISTING

The instant application contains a Sequence Listing which has been submitted in ASCII format via EFS-Web and is hereby incorporated by reference in its entirety. Said ASCII copy, modified on Aug. 31, 2020 is named "NC105743CIP_ST25.txt" and is 2.0 kilobytes in size.

FIELD OF THE INVENTION

The subject matter of the instant invention relates to methods of treating a fungal infection in a subject in need thereof comprising administering to the subject a therapeutically effective amount of a composition comprising one or more peptides selected from the group consisting of BmKn2, dBmKn2, Kn2-7, and dKn2-7. Antifungal compositions comprising one or more of these peptides are also contemplated herein.

BACKGROUND OF INVENTION

Fungal infections are difficult to eradicate and can rapidly evolve into invasive and/or systemic disease. These infections require long treatment durations and are associated with high morbidity and mortality, especially in certain populations such as immunocompromised, neonate, and burn patients. Species of *Candida* are the most common cause of fungal infections, and invasive candidiasis has reported mortality rates of 14-70% (Macherla, C., et al., Front. Microbiol. 2012, 3:193). In addition, interaction of *Candida albicans* with bacteria in polymicrobial wound infections results in increased virulence compared to monomicrobial infections. Co-infection with *Staphylococcus aureus* and *C. albicans* in mice, for instance, causes a synergistic increase in virulence and mortality relative to infection with *S. aureus* alone. (Hamilton, J. R., et al., Infect. Immun., 1976, 14(4):982-9.)

Fungi are eukaryotes and thus existing antifungal therapeutics may attack similar molecular targets on mammalian cells, resulting in severe side-effects and dosing limitations. Moreover, the formation of biofilms by pathogenic fungal species may result in a significant decrease in susceptibility to conventional antifungal agents. These challenges are exacerbated by the rise of drug resistant *Candida* species, the limited number of clinically approved antifungals, and the low number of new antifungal drugs in the pipeline for pharmaceutical development. Thus, there currently remains a need for new antifungal agents and methods of treating fungal infections.

SUMMARY OF THE INVENTION

In a first aspect, the invention relates to methods of treating a fungal infection in a subject in need thereof comprising administering to the subject a therapeutically effective amount of a pharmaceutical composition comprising one or more peptides selected from the group consisting of BmKn2, dBmKn2, Kn2-7, and dKn2-7. In one embodiment, the peptides comprise D-form amino acids. In another embodiment, the fungal infection is a planktonic or a biofilm fungal infection, or a combination thereof. In a particular embodiment, the biofilm fungal infection comprises a pre-formed biofilm. In another embodiment, the fungal infection is resistant to one or more conventional antifungal agents. In another embodiment, the fungal infection is a wound infection.

In another aspect, the invention relates to methods of treating a polymicrobial infection in a subject in need thereof comprising administering to the subject a therapeutically effective amount of a pharmaceutical composition comprising one or more peptides selected from the group consisting of BmKn2, dBmKn2, Kn2-7, and dKn2-7. In one embodiment, the peptides comprise D-form amino acids. In a particular embodiment, the polymicrobial infection comprises a planktonic or a biofilm fungal infection, or a combination thereof. In a particular embodiment, the biofilm fungal infection comprises a pre-formed biofilm. In another embodiment, the polymicrobial infection comprises a fungal infection which is resistant to one or more conventional antifungal agents. In another embodiment, the polymicrobial infection is a wound infection.

In various embodiments of the above aspects, the methods of the instant invention may comprise administering the pharmaceutical composition alone, or in combination with a therapeutically effective amount of one or more additional pharmaceutically acceptable agents. In one embodiment, the one or more additional pharmaceutically acceptable agent is selected from the group consisting of an antimicrobial agent, an analgesic, a wound healing agent, a biofilm dispersal agent and a biofilm inhibitor agent. In a particular embodiment, the antimicrobial agent is an antifungal, antibacterial, or antiviral agent.

In yet additional aspects, the invention relates to anti-polymicrobial and anti-fungal compositions comprising one or more peptides selected from the group consisting of Kn2-7, dKn2-7, BmKn2, and dBmKn2. In a particular embodiment, the composition is a pharmaceutical composition comprising said one or more peptides. In a particular embodiment, said one or more peptides are present in an amount sufficient to treat a fungal infection in a subject in need thereof. In a particular embodiment, said amount is from about 6 µg/mL to about 5 mg/mL of said one or more peptides. In a particular embodiment, the pharmaceutical composition further comprises one or more pharmaceutically acceptable carriers, excipients or diluents. In particular embodiments, the pharmaceutical composition comprises one or more additional pharmaceutically acceptable agents. In one embodiment, the one or more additional pharmaceutically acceptable agent is selected from the group consisting of an antimicrobial agent, an analgesic, a wound healing agent, a biofilm dispersal agent and a biofilm inhibitor agent. In a particular embodiment, the antimicrobial agent is an antifungal, antibacterial, or antiviral agent.

In another aspect, the invention relates to dosage forms comprising a pharmaceutical composition of the instant invention. In one embodiment, the dosage form is formulated for topical administration. In a particular embodiment, the dosage form is a wound dressing. In a more particular embodiment, the wound dressing is a field-deployable wound dressing.

In additional aspects, the invention also includes use of a composition of the instant invention for treating a fungal infection in a subject in need thereof, use of a composition of the instant invention in the manufacture of a medicament for treating a fungal infection in a subject in need thereof, and use of the compositions of the instant invention for use in treating a fungal infection in a subject in need thereof.

DETAILED DESCRIPTION

Figure 1:
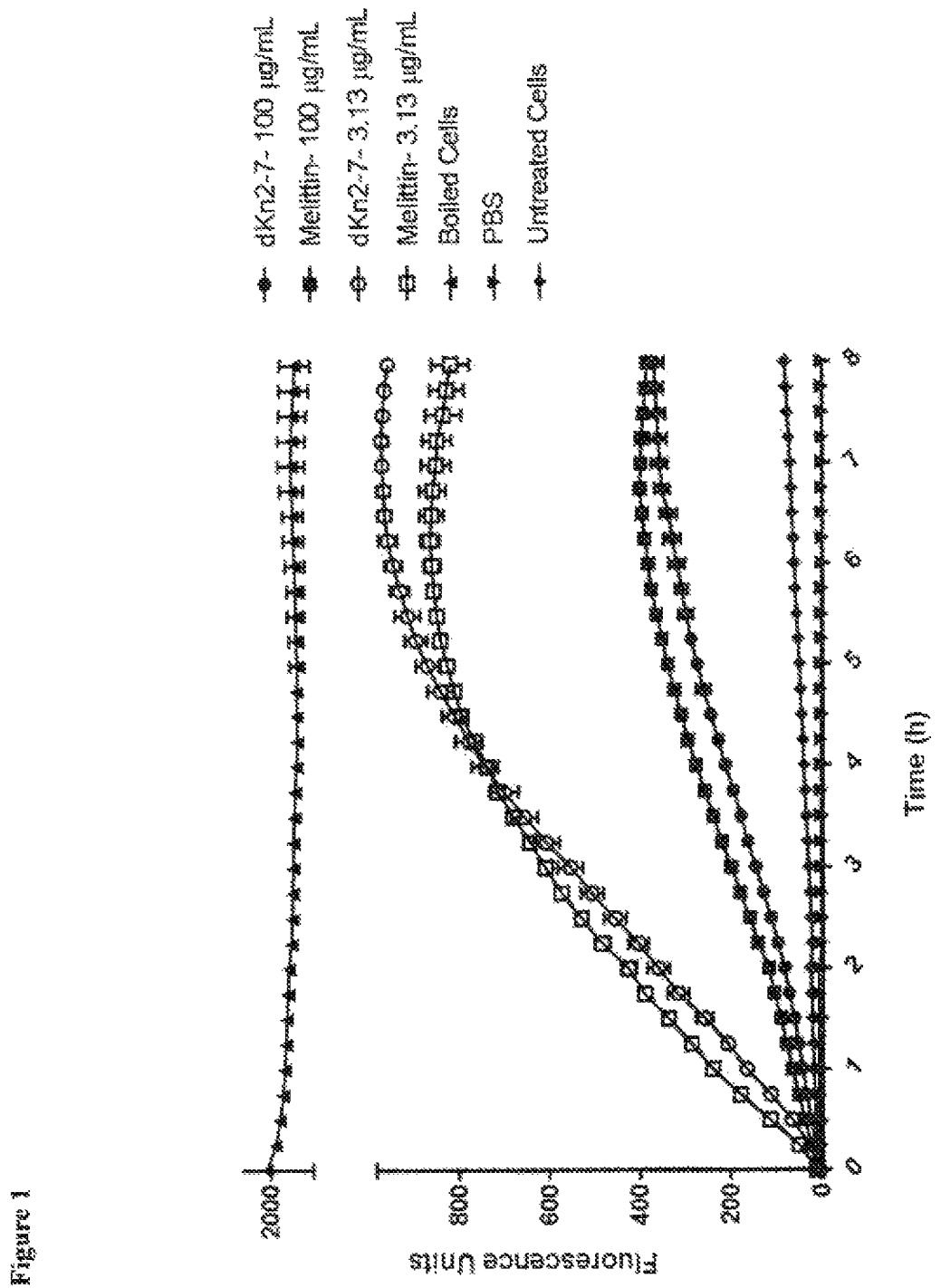
FIG. 1 depicts the time-dependent release of calcein AM (in hours) from MYA 2876 C. albicans cells treated with dKn2-7 or melittin. Samples were analyzed via fluorescence spectroscopy using a Tecan Spark 10M microplate reader (Tecan U.S., Morrisville, N.C.), and results are presented in fluorescence units. Closed circles represent dKn2-7 100 µg/mL; closed squares represents melittin 100 µg/mL; open circles represent dKn2-7 3.13 µg/mL; open squares represent melittin 3.13 µg/mL; triangles represent boiled cells; upside down triangles represent phosphate buffered saline (PBS) alone without cells; diamonds represent untreated cells in PBS.

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include components in addition to those recited in the claim, but only if the additional components do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a pharmaceutically acceptable agent" can mean at least one pharmaceutically acceptable agent, as well as a plurality of pharmaceutically acceptable agents, i.e., more than one pharmaceutically acceptable agent.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

The venom of the scorpion *Mesobuthus martensii* Karch comprises the peptide BmKn2. BmKn2 is a 13 amino acid peptide having the sequence FIGAIARLLSKIF (SEQ ID NO. 1). Kn2-7, an experimental derivative of BmKn2, has the amino acid sequence FIKRIARLLRKIF (SEQ ID NO. 2). These peptides reportedly have some antibacterial and antiviral activity. See, Zeng X C, et al., (2004) Peptides 25: 143-150; Cao et al., (2012) PLoS ONE 7(7): e40135.

The inventors have now discovered that BmKn2 and Kn2-7 peptides have anti-fungal activity. Specifically, as discussed in the Examples below, the inventors have discovered that the BmKn2 and Kn2-7 peptides (both "D" and "L" forms) have growth inhibitory, fungicidal, and anti-biofilm activity in in vitro models of *Candida albicans*. The inventors believe that this discovery is of particular and surprising clinical relevance since one of skill in the art will appreciate that not all antimicrobial peptides derived from scorpion venoms demonstrate antifungal activity. Thus, it is contemplated herein that these antifungal peptides may be used in compositions and methods for killing fungi, and/or inhibiting fungal growth, including but not limited to, pharmaceutical compositions comprising one or more of these antifungal proteins, and methods of treating fungal infections in a subject in need thereof, including, e.g., biofilms and/or planktonic infections in a subject.

The antifungal peptides disclosed herein may be obtained for use in the methods and compositions of the instant invention according to conventional methods. For example, the peptides may be routinely isolated from the scorpion *Mesobuthus martensii* Karsch, and/or synthetically produced using methods familiar to one of skill in the art. In addition, as discussed in detail in the below Examples, the inventors have also observed that when experimentally synthesized to comprise "D" form amino acids, the BmKn2 and Kn2-7 peptides have increased stability. Thus, in various embodiments of the methods and compositions of the instant invention, it is contemplated herein that the BmKn2 and Kn2-7 peptides may be synthetically produced using conventional methods to comprise all "D" amino acids" (e.g., "dBmKn2" and "dKn2-7"), all "L" amino acids, or a combination of "D" and "L" amino acids. As understood herein, "Kn2-7 and BmKn2" refers to the peptides comprising "L" form amino acids or a combination of "D" and "L" form amino acids; as used herein "dBmKn2" and "dKn2-7" refers to the peptides comprising "D" but not "L" form amino acids. In a particular embodiment, the peptides comprise all "D" form amino acids.

In another embodiment, the peptides are free of protecting groups, and have free amino and carboxy termini. In various other embodiments, the peptides may comprise alternative unnatural amino acids including but not limited to, homoamino acids, N-methyl-amino acids, alpha-methyl amino acids, beta 2 amino acids, beta 3-homo amino acids, and peptoids. As one of skill in the art will appreciate, routine single or multiple substitutions of peptide amino acids which do not appreciably impact the efficacy of the peptides are also contemplated herein, e.g., substitution of a positively charged amino acid like lysine with arginine.

In addition, it is contemplated herein that the peptides may be modified at the N or C terminus by conjugation to various things, e.g., targeting ligands such as antibodies to increase cell selectivity and reduce host cell toxicity; nanoparticles composed of metallic and non-metallic substances such as gold, silver, polymers, or silica; other nonmetal nanoparticles such as dendrimers; lipophilic groups such as cholesterol or vitamin E; aliphatic acids to increase antifungal activity; photosensitizers; or antifungal antibiotics. The peptides can also be immobilized onto various materials or surfaces, e.g., collagen matrices, or incorporated into coatings for surfaces or into biomaterials used for tissue matrices, catheters, and other medical or dental implants and devices.

In one aspect, the present invention relates to methods of treating a fungal infection in a subject in need thereof comprising administering to the subject a therapeutically effective amount of a composition comprising one or more peptides selected from the group consisting of dKn2-7, dBmKn2, Kn2-7 and BmKn2. In one embodiment, the BmKn2 and Kn2-7 peptides comprise "L" form amino acids, "D" form amino acids, or a combination of "D" and "L" form amino acids. In a particular embodiment, the peptides are dKn2-7 and dBmKn2, comprising "D" form amino acids. In a particular embodiment, the composition is a pharmaceutical composition.

Thus, in another aspect, the invention relates to pharmaceutical compositions which comprise one or more of these antifungal peptides, alone or in combination with one or more additional pharmaceutically acceptable agents, and in combination with one or more pharmaceutically acceptable excipients, carriers, or diluents.

As understood herein, the term "pharmaceutically acceptable" is used to refer to a non-toxic material that is compatible with a biological system such as a cell, cell culture, tissue, or organism.

Examples of pharmaceutically acceptable excipients, carriers and diluents are familiar to one of skill in the art and can be found, e.g., in Remington's Pharmaceutical Sciences (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable excipients, carriers and diluents included in the pharmaceutical compositions of the instant invention may vary, e.g., depending upon the desired route of administration and desired physical state, solubility, stability, and rate of in vivo release of the composition. For example, for administration by intravenous, cutaneous, subcutaneous, or other injection, a formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art.

"Additional pharmaceutically acceptable agents" for use in the methods and compositions of the instant invention are familiar to one of skill in the art and include, e.g., a variety of commercially available active pharmaceutical ingredients, including but not limited to, additional antimicrobials such as antifungal, antibacterial, and/or antiviral agents discussed below.

In a particular embodiment, the fungal infection is a planktonic or a biofilm fungal infection, or a combination thereof. For example, it is contemplated herein that a wound may comprise biofilm-associated and loose or free fungal cells.

In a particular embodiment, the biofilm fungal infection comprises a pre-formed biofilm. As one of skill in the art will appreciate, therapeutic efficacy against a "pre-formed" biofilm indicates activity against an established biofilm culture versus activity against de novo biofilm formation (e.g., inhibition of biofilm formation). In another embodiment, the fungal infection is resistant to one or more conventional antifungal agents.

It is contemplated herein that infections caused by a wide variety of pathogenic fungi may be treated according to the methods of the instant invention, including fungal infections that may be resistant to one or more conventional antifungal agents. In a particular embodiment, fungi to be treated include, but are not limited to, pathogenic species such as: *Aspergillus; Blastomyces; Candida; Fusarium; Trichosporon; Penicillium; Coccidioides; Cryplococcus neoformans; Cryptococcus gattii; Histoplasma; Mcorales; Pneumocysis; Sporthrix; Trichophylon, Microsporum, Epidermophyton, Exserohilum*, and *Cladosportum*.

In a particular embodiment, the infection to be treated is a fungal infection, and/or a polymicrobial infection. As understood herein, a "polymicrobial infection" may comprise infection with one or more pathogenic fungi in addition to infection with one or more additional microbes, e.g., bacteria and/or viruses.

In a particular embodiment, the infection to be treated is a wound infection. As understood herein, a "wound" refers to external or internal tissue that has been incised, lacerated, perforated, abraded, burnt or otherwise degraded, and includes acute wounds, chronic wounds, as well as minor cuts and burns. In a particular embodiment, the wounds to be treated are cutaneous and/or subcutaneous wounds. As contemplated herein, the antifungal compositions and methods of the instant invention can be used to treat fungal infections, and thus promote wound healing.

As used herein, "treating", "treatment", and like terms encompass reducing the severity and/or frequency of symptoms, eliminate symptoms and/or their underlying cause, prevent the occurrence of symptoms and/or their underlying cause, and improve or remediate damage. As understood herein, treating "a subject in need thereof" may encompass both prevention and treatment. Thus, in a particular embodiment, "treating" encompasses not only killing fungi (e.g., a planktonic or a biofilm fungal infection, or a combination thereof) but also inhibiting the growth and/or proliferation of fungi and/or inhibiting the formation, growth or maintenance of a biofilm comprising fungi.

As used herein, "a subject in need thereof" includes an animal, including but not limited to birds and mammals, suffering from and/or susceptible to one or more fungal infections, and/or a polymicrobial infection which comprises one or more fungal infections. Human beings are also encompassed in this term. In particular, subjects in need thereof include, but are not limited to, domesticated animals as well as non-human primates and human patients.

As used herein, one of skill in the art will appreciate that a "therapeutically effective amount" of a pharmaceutical composition of the instant invention is that amount necessary to achieve a desired pharmacologic and/or physiologic effect in a subject (by local and/or systemic action), e.g., killing or inhibiting fungal growth in the subject. Such amounts can be readily determined by one of skill in the art. For example, therapeutically effective amounts of a pharmaceutical composition may be gleaned by one of skill in the art in laboratory experiments, and through conventional dosing trials and routine experimentation. Therapeutically effective amounts of the pharmaceutical compositions of the instant invention may depend upon the age, weight, species (if non-human) and medical condition of the subject to be treated, and whether the antifungal peptides are administered alone or in combination with one or more additional pharmaceutically acceptable agents, e.g., an antimicrobial agent, including but not limited to one or more additional antifungal agents.

As discussed above, it is contemplated herein that the anti-fungal peptides may be administered in various way according to the methods of the instant invention, e.g., alone or in combination with one or more additional pharmaceutically acceptable agents, therapeutic treatments, or regimens, in order to enhance treatment efficacy. As one of skill in the art will appreciate, the type and amount of additional pharmaceutically acceptable agents, therapeutic treatments or regimens for use in the methods and compositions of the instant invention will depend upon the type of infection to be treated; e.g., an infected wound may be treated with one or more antifungal peptides disclosed herein alone, or in conjunction with one or more other pharmaceutically acceptable antimicrobial compounds, as well as surgical drains, bandages, etc. which may be conventionally used for treating wounds. In a particular embodiment, it is contemplated herein that the anti-fungal peptides can be combined in a single formulation with one or more other classes of pharmaceutically acceptable agents, e.g., antifungals, antibacterials, antivirals, analgesics, or wound healing agents to enhance treatment efficacy.

It is contemplated herein that a therapeutically effective amount of said one or more additional pharmaceutically acceptable agents for conventional use are familiar to one of skill in the art; amounts for use in the methods and compositions of the instant invention may also be readily determined by one of skill in the art according to conventional methods. In one embodiment, it is contemplated herein that therapeutically effective amounts of an additional pharmaceutically acceptable agent, e.g., a conventional antimicrobial, antifungal, or antiviral agent, may be reduced when administered in combination with one or more of the anti-fungal peptides disclosed herein (or vice versa). In addition, it is also contemplated herein that when said one or more additional pharmaceutically acceptable agents is administered in conjunction with one or more antifungal peptides disclosed herein, the agent may only need to be administered to a subject for a fraction of the time that said agent would typically need to be administered when administered alone (and vice versa).

As understood herein, "antifungals" for use in the methods and compositions of the instant invention include a variety of conventional topical and systemic agents that can kill, inhibit and/or otherwise control fungal growth. Such products are familiar to one of skill in the art and are available from a variety of commercial vendors, and include, but are not limited to antifungal drugs such as azoles, echinocandins, nucleoside analogs, and polyenes. Such compounds include, e.g.: tolnaftate; amorolfine; ciclopirox olamine; flucytosine; griseofulvin; haloprogrin; potassium iodide sodium pyrithione; undecylenic acid; bifonazole, butoconazole, clotrimazole, isoconazole, tioconazole, econazole, ketoconazole, miconazole, oxiconazole, sertaconazole, sulconazole, itraconazole, fluconazole, terconazole; voriconazole; naftifine, butenafine, and terbinafine. Antifungal antibiotics include amphotericin B, caspofungin, anidulafungin, micafungin, and nystatin. Therapeutically effective amounts for conventional use are familiar to one of skill in the art.

Similarly, "antibacterials" are products that can destroy or inhibit the growth of bacteria and are familiar to one of skill in the art. Antibacterial agents suitable for pharmaceutical use include a variety of agents, e.g., from groups such as penicillins, cephalosporins, glycopeptide derivatives, carbopenems, aminoglycosides, macrolides, tetracyclines, chloramphenicol, lincomycins, sulfonamides, metronidazole, pyrimidine derivatives, rifampicin, and quinolones. In a particular embodiment, antibacterial agents for use in the methods and compositions of the instant invention include, e.g., amikacin, gentamicin, tobramycin, meropenem, imipenem, cefazolin, cefepime, cefoxitin, cephalothin, ceftazidime, cefotaxime, cefoperazone, ceftriaxone, cefuroxime, levofloxacin, ciprofloxacin, nitrofurantoin, trimethoprim-sulfamethoxazole, linezolid, vancomycin, erythromycin, clindamycin, daptomycin, mupirocin, ampicillin, piperacillin, oxacillin, penicillin, mezlocillin, amoxicillin, aztreonam, sulfosoxazole, chloramphenicol, streptomycin, tetracycline, minocycline, rifampin, and silver sulfadiazine. Such products are commercially available in a variety of forms from a variety of vendors, and therapeutically effective amounts for conventional use are familiar to one of skill in the art.

"Antiviral agents" contemplated for use in the methods and compositions of the instant invention include, e.g., a variety of commercially available pharmaceutical agents which can inhibit viral growth. These include, e.g., penciclovir, acyclovir, famciclovir, valacyclovir, tenofovir disoproxil fumarate, lamivudine, zidovudine, didanosine, emtricitabine, stavudine, nevirapine, abacavir, raltegravir, dolutegravir, darunavir, ritonavir, cobicistat, and efavirenz. Therapeutically effective amounts for conventional use are familiar to one of skill in the art.

In addition to the foregoing antimicrobial agents, one of skill in the art will appreciate that additional pharmaceutically acceptable agents include a variety of topical or systemic pharmaceutical agents which may be used to treat fungal and/or polymicrobial infections. These include, but are not limited to, commercially available products that facilitate wound healing which are familiar to one of skill in the art, e.g., pharmaceutical formulations comprising chitosan, antiseptics, antioxidants, vitamins, minerals, debriding agents, irrigants, hydrocolloids, alginates, hydrofibers, sodium chloride gels, hydroactive pastes, zinc, silver and/or comprising cell proliferating agents such as growth factors, e.g., epidermal growth factor, keratinocyte growth factor, transforming growth factors, vascular endothelial growth factor, platelet-derived growth factor; collagen, biological dressings and skin equivalents, keratinocytes, fibroblasts, platelet-rich plasma, honey, curcumin, papain, and bromelain. Additional pharmaceutically acceptable agents for use in the pharmaceutical compositions and methods of the instant invention also include, but are not limited to, compounds that reduce pain, e.g., analgesics; anesthetics; and anti-inflammatory agents; compounds that are hemostatic agents, and compounds that are immunomodulators.

In addition, it is contemplated herein that the antifungal peptides of the instant invention could be used in combination with one or more fungal biofilm dispersal agents or inhibitors of biofilm formation. Such dispersal or inhibitor agents are familiar to one of skill in the art and include, but are not limited to substances such as nitric oxide, cis-2-decenoic acid, quorum sensing molecules such as farnesol, and enzymes such as DNAse, β-glucanase, bromelain, and papain.

As discussed above, one of skill in the art will appreciate that the antifungal peptides of the instant invention may be administered alone, or in combination with one or more additional pharmaceutically acceptable agents, therapeutic treatments or regimens discussed herein, in any manner or combination that may be deemed therapeutically effective, e.g., before, after, or concurrently with the antifungal peptides of the instant invention; separately in different formulations and dosage forms; at different times, and/or routes of administration, or in combination with the antifungal peptides in a single formulation.

Various compositions, formulations, and dosage forms designed to treat fungal infections in a subject in need thereof are contemplated herein, and may be created according to conventional methods by one of skill in the art. Indeed, it is contemplated herein that pharmaceutical compositions and dosage forms may be administered to a subject by a variety of routes according to conventional methods, including but not limited to parenteral (e.g., by intracisternal injection and infusion techniques), intradermal, transmembranal, transdermal (including topical), ocular, intramuscular, intraperitoneal, intravenous, intra-arterial, intralesional, subcutaneous, oral, and intranasal (e.g., inhalation) routes of administration. Administration can also be by continuous infusion or bolus injections. Such compositions, formulations, dosage forms, and methods of delivery may be suitable for treating fungal infections, e.g., on the skin, in the bloodstream, deep tissue, oral cavity, ocular cavity, gastrointestinal tract, urinary tract or any other location in a subject in which a fungal infection may be present.

Dosage forms contemplated herein include but are not limited to immediate release as well as modified release dosage forms. Such dosage forms, and methods of formulating such dosage forms, are familiar to one of skill in the art. Examples of modified release dosage forms include, e.g., controlled-release, extended-release, targeted-release, and timed-release dosage forms, e.g., comprising the use of microcapsules and other conventional methodologies familiar to one of skill in the art. In particular embodiments, dosage forms contemplated herein include topical dosage forms that provide immediate release and/or modified release of one or more anti-fungal peptides disclosed herein, including but not limited to controlled-release, extended-release, and timed-release formulations for topical application.

The term "dose", "dosage", "dosage form" and like terms used herein refer to physically discrete units suitable for administration to a subject, each dosage comprising a predetermined quantity of antifungal peptides as an active pharmaceutical ingredient calculated to produce a desired response. As contemplated herein, the pharmaceutical compositions of the instant invention are preferably sterile and contain an amount of the antifungal peptides in a unit of weight or volume suitable for administration to a subject.

The formulation and creation of dosage forms of the instant invention may be achieved by one of skill in the art using conventional methods. For example, the weight or volume of the composition administered to a subject will depend on the method of administration and is discernible by one of skill in the art. For instance, in the case of an injectable, the volume administered typically may be between about 0.1 ml and 1.0 ml, preferably approximately 0.5 ml. In addition, one of skill in the art will appreciate that, depending on the efficiency of release of a particular dosage form, the dosage amount loaded into a dosage form may be greater than the amount designed to be released and delivered to the subject in order to deliver a therapeutically effective amount of active agent(s). For example, this may be the case with dosage forms such as a gauze bandage, patch, or hydrogel.

Therapeutically effective amounts of the peptides may vary, and can be ascertained by one of skill in the art without undue experimentation. In particular embodiments, it is contemplated herein that a therapeutically effective amount of an anti-fungal peptide of the instant invention may range from about 6 µg/mL to about 5 mg/mL. For example, in various particular embodiments, based on in vitro efficacy (MICs and MFCs) and toxicity (hemolysis) data, it is contemplated herein that, about 6-100 µg/mL of Kn2-7 and/or dKn2-7 peptides may be suitable for systemic antifungal therapy (e.g., planktonic blood stream infections). In addition, with regard to topical therapy (e.g., planktonic and biofilms) and assuming minimal toxicity to skin cells at 5 mg/mL (Cao et al. (2012), PLoS ONE, 7(7):e40135), it is contemplated herein that about 6-500 µg/mL of dKn2-7 and/or about 12.5-1000 µg/mL of Kn2-7 may be used for anti-fungal therapy.

In additional various embodiments, MIC/MFC and hemolysis data for BmKn2 and dBmKn2 suggest that, for systemic (planktonic) infections, about 25-50 µg/mL BmKn2 and/or dBmKn2 could be used in vivo, while about 25-500 µg/mL dBmKn2 may be suitable for topical administration against planktonic and/or biofilm infections. Additional therapeutically effective amounts of the peptides for clinical use can be ascertained by one of skill in the art without undue experimentation.

Dosage forms include, in a particular embodiment, dosage forms for topical administration to a subject in need thereof. These types of dosage forms are familiar to one of skill in the art and include, for example, dosage forms to be applied to the skin and/or for ocular administration. Dosage forms suitable for topical administration of the pharmaceutical compositions of the instant invention may be created by one of skill in the art using conventional methods. These include, but are in no way limited to, creams or ointments, or other topical pharmaceutical compositions, e.g. in the form of emulsion-gels. Topically acceptable carriers, excipients, and diluents for use in such formulations are familiar to one of skill in the art and include, e.g., aqueous phases, oily phases, emulsions, hydrogels, pastes, liposomal formulations, nanoparticle formulations, foams, powders, and spray-on formulations.

Dosage forms in the form of patches, films, and bandages comprising the antifungal peptides are also contemplated herein. Indeed, the short antifungal peptides disclosed herein do not require a tertiary structure to perform their microbicidal activity. Thus, the peptides can remain stable under inert, room temperature conditions, making them suitable for inclusion within a wound dressing with good performance and long shelf life.

Moreover, in a particular embodiment, it is contemplated herein that D-amino acid forms of the antifungal peptides may be used to increase stability of the peptides against proteases (fungal as well as proteases in wound exudate, blood, etc.) in these dressings and when used in other dosage forms.

Thus, in a particular embodiment, it is contemplated herein that the antifungal peptides of the instant invention may be incorporated in materials suitable for dressing wounds according to methods familiar to one of skill in the art. For example, the antifungal peptides disclosed herein may be used in the manufacture of antimicrobial dressings. In a particular embodiment, it is contemplated herein that these peptides can be electrospun into fibers by one of skill in the art according to conventional methods as a method to create antimicrobial dressings comprising these antifungal peptides. See, e.g., Heunis, T. D. J., & Dicks, L. M. T. "Nanofibers Offer Alternative Ways to the Treatment of Skin Infections" *BioMed Research International*, (*Journal of Biomedicine and Biotechnology*) Volume 2010 (2010), Article ID 510682, 10 pages; Heunis, T. D., et al. (2013) *Antimicrobial Agents and Chemotherapy*, 57(8), 3928-3935; Heunis, T., et al. (2011) *International Journal of Molecular Sciences*, 12(4), 2158-2173; Sebe, I., et al., (2016) *Amino Acids*, 48(1), 203-211; Eriksen, T. H. B., et al. (2013) *Journal of Biomedical Nanotechnology*, (3), 492-498; the contents of all of which are incorporated by reference herein in their entirety.

In addition to electrospinning techniques, it is further contemplated herein that wet-spinning methods familiar to one of skill in the art may be used to create fibers for use in dressings of the instant invention. Wet-spinning techniques offer some advantages over electrospinning, e.g., electrospinning typically requires the use of volatile organic solvents which are often toxic, expensive, and can add contaminates to the formulations. In contrast, wet-spinning of fibers from sodium alginate and chitosan such as disclosed herein (see Example 10) uses aqueous salt solutions for the formulation which are less toxic and less expensive. Moreover, as evidenced herein, peptides Kn2-7 and dKn2-7 are reasonably stable in aqueous solutions. Electrospinning is harder and more expensive to scale up for large-scale manufacturing as it relies on rapid evaporation of organic solvents from small output streams (and is therefore also prone to issues with reproducibility due to environmental conditions such as temperature and humidity), whereas wet-spinning is a common practice for large-scale manufacturing of reproducible fibers (e.g., rayon, spandex, alginate, etc.)

Additionally, just as voltage, extrusion rate, and solvent changes can be used to switch from electrospinning to electrospraying (i.e., from fibers to microspheres), it is contemplated herein that changes to wet spinning formulations can also be made to result in microsphere formulations. Therefore, it is contemplated herein that both methods would allow the formation of either fibers for a wound dressing (e.g., similar to gauze), or a powder that can be sprinkled as needed into a wound (e.g., similar to sulfonamide).

As discussed above, topical dressings and other dosage forms of the instant invention may comprise other pharmaceutically acceptable agents, including but not limited to, other pharmaceutically active antimicrobial agents, wound healing agents, analgesics, and/or anti-inflammatory compounds. In particular embodiments, such topical dressings and other dosage forms may be used, for example, to treat polymicrobial infections, e.g., bacterial-fungal polymicrobial infections, including but not limited to, infections that may be resistant to one or more conventional anti-microbial drugs.

Also contemplated herein are dosage forms that are liquid preparations and suspensions, including, preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the antifungal compositions of the instant invention are administered to a subject as an injectable, including but not limited to injectable compositions for delivery by intramuscular, intravenous, subcutaneous, or transdermal injection. Such compositions may be formulated using a variety of pharmaceutical excipients, carriers or diluents familiar to one of skill in the art.

Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate. A composition for oral administration may be a liquid formulation. Such formulations may comprise a pharmaceutically acceptable thickening agent which can create a composition with enhanced viscosity which facilitates mucosal delivery of the peptide(s), e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. The antifungal peptides and other active pharmaceutical ingredients in the compositions of the instant invention may also be lyophilized and may be delivered to a subject with or without rehydration using conventional methods.

In a particular embodiment, the dosage forms contemplated herein include field-deployable dosage forms. As used herein, "field-deployable dosage forms" include dosage forms that can be used at the point of need with minimal requirements for additional resources, e.g., in locations which are removed from a full-service clinic. In a particular embodiment, these locations include, e.g., locations on a battlefield or other remote situations distant from military or other conventional healthcare systems. In a particular embodiment, a dosage form of the instant invention may be a topical wound dressing comprising one or more of the antifungal peptides of the instant invention. Such topical wound dressing may be manufactured in the form of a field-deployable dosage form such as a gauze, patch, film, bandage, powder, or wound packing product or filler such as foams, beads, pillows, and strands. The dosage form could also be a suture, wound irrigant, dry powder inhalant, or easy-to-use injection such as from an autoinjector. It is contemplated herein that in various particular embodiments, amounts of the peptides for topical use in a field deployable wound dressing may range from about 6-1000 µg/mL.

In particular embodiments, dosage forms which provide a delivery method that ensures peptide concentrations stay within a therapeutic range for an extended period of time (e.g., at least 24 hours) are also contemplated herein. As understood herein, such therapeutic levels would provide a continuing clinical benefit and would not be provided at levels toxic to mammalian cells. As discussed above, with regard to topical therapy (e.g., planktonic and biofilms) and assuming minimal toxicity to skin cells at 5 mg/mL (Cao et al. (2012), PLoS ONE, 7(7):e40135), it is contemplated herein that about 6-500 µg/mL of dKn2-7 and/or about 12.5-1000 µg/mL of Kn2-7 may be used for anti-fungal therapy.

In particular, stable, antimicrobial wound dressings for topical infections which provide modified release, including but not limited to controlled and/or extended release, of therapeutic levels of scorpion venom peptides disclosed herein are contemplated. As contemplated herein, in particular embodiments, these wound dressings may further comprise additional therapeutic agents, e.g., materials that are known to have additional properties advantageous in wound healing, such as disclosed herein.

It is contemplated herein that immediate as well as modified release, e.g., controlled and extended release, dosage forms of the instant invention may be created by one of skill in the pharmaceutical arts using conventional methods to formulate peptide loading and release rates as desired, e.g., by adjusting formulation morphology and/or fiber composition. For example, in some embodiments, it is contemplated herein that electrospinning and/or wet-spinning techniques may be used to create immediate and/or modified release, e.g., controlled and extended release, dosage forms of the instant invention. Such dosage forms include topical dressings, including topical wound dressings for field use.

In particular embodiments, it is contemplated herein that alginate, chitosan, and alginate/chitosan blends may be used with such methods to create various types of dosage forms of the instant invention. For example, both polysaccharides are water-soluble and can be formulated into multiple types of structures using aqueous-based, polyelectrolyte complexation techniques such as solvent casting (films), wet-spinning (fibers), and homogenization (microspheres). These techniques also permit the incorporation of other charged substances (including, e.g., other antimicrobial peptides) into the formulations.

Thus, in various embodiments, the instant invention relates to polysaccharide fibers impregnated with the synthetic scorpion venom-derived antimicrobial peptides disclosed herein. In a particular embodiment, the peptide is dKn2-7. In certain embodiments, the polysaccharides used in the fibers are alginate and chitosan.

In another embodiment, it is contemplated herein that polysaccharides can be solubilized in an aqueous solution and added to a separate aqueous solution of calcium chloride to create ionic hydrogels. By modifying the method of mixing the two solutions, fibers or microspheres can be created. In a particular embodiment, it is contemplated herein that the peptides of the instant invention, including but not limited to dKn2-7 can be incorporated into the formulation, e.g., either by adding the peptide to the initial polysaccharide solution before the formulation or by soaking the fibers/microspheres in an aqueous peptide solution after formulation. See Example 10 below. It is believed that the ionic interaction between polycationic peptides, e.g., dKn2-7, and the polyanionic alginate may help facilitate peptide loading and binding. Incorporation of the polycationic chitosan and calcium chloride may introduce ionic competition for the peptide for the negative charges on the alginate molecules, thereby modulating the potential peptide loading and binding strength of the peptide. These properties may be used to control peptide release from the formulations.

In addition to treating topical wound infections, it is also contemplated herein that topical dosage forms and other dosage forms of the instant invention, including but not limited to the extended and controlled release dressings and dosage forms contemplated herein, may be used by one of skill in the art to treat infections and bleeding associated with burns, open ulcers, surgical incisions and wounds, deep wounds, cavity wounds, sinuses, and other body cavities such as the oral cavity, nasal cavity, ocular, etc.

As understood herein, the methods of the instant invention include methods comprising administering a pharmaceutical composition to a subject in need thereof according to various regimens, i.e., in an amount and in a manner, and for a time sufficient to provide a clinically meaningful benefit to the subject. Suitable administration regimens for use with the methods of the instant invention may be determined by one of skill in the art according to conventional methods. For example, it is contemplated herein that a therapeutically effective amount of antifungal peptides may be administered to a subject as a single dose, or a series of multiple doses administered over a period of days. For example, a pharmaceutical composition of the instant invention may be applied topically at least once a day, but more frequent daily applications are contemplated herein.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular composition. One of skill in the art will appreciate that in some cases, a "therapeutically effective amount" may encompass more than one administered dosage amount.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1: Synthesis of BmKn2 and Kn2-7
Peptides Comprising D or L Amino Acids

Peptides comprising either L or D isomers were synthesized by GenScript (Piscataway, N.J., USA) and purified to homogeneity using reverse phase-high pressure liquid chromatography. Peptide structure was confirmed using electrospray ionization mass spectrometry.

As provided in the below examples, data indicate that the anti-fungal activity of BmKn2 and Kn2-7 is increased by converting the naturally occurring L-amino acids to D-forms. We hypothesize that this change may decrease the susceptibility of the peptides to proteases secreted by the fungi. Additionally, the in vivo bioavailability and efficacy may be improved by converting the amino acids in the peptides from L- to D-form. Thus far we have found that dKn2-7 has the most potent activity with minimum inhibitory concentrations (MICs) and minimum fungicidal concentrations (MFCs) as low as 6.25 µg/mL and 12.5 µg/mL, respectively. We have also found that this peptide can completely inhibit the metabolic activity of pre-formed biofilms at concentrations between 62.5 and 125 µg/mL. This peptide demonstrates better activity compared to the well-studied LL-37 peptide, which has ~3x higher MIC against *C. albicans*.

Example 2: Minimum Inhibitory Concentration (MIC) and Minimum Fungicidal Concentration (FC) Data for *Candida albicans* Treated with BmKn2, dBmKn2, Kn2-7, or dKn2-7 Peptides Laboratory strains (MYA 2876 and ATCC 64124) (American Type Culture Collection, Manassas, Va., USA) and three clinical isolates (CA494, CA526, and CA2519) (San Antonio Military Medical Center, Joint Base San Antonio-Fort Sam Houston, Tex., USA) of *C. albicans* were tested. MICs were determined by treating planktonic cultures with various concentrations of the peptides for 24 hours at 37° C. and then reading the absorbance of the samples at 600 nm. The MIC was the lowest peptide concentration that showed no absorbance reading above background (lack of growth). MFCs were determined by treating planktonic cultures with various concentrations of the peptides for 48 hours at 37° C., plating the samples on Sabouraud-Dextrose agar plates (Hardy Diagnostics, Santa Maria, Calif., USA), incubating the plates for 24 hours at 37° C., and visually inspecting the plates for fungal growth. The MFC was the lowest peptide concentration that showed no growth of fungal colonies. Overall, dKn2-7 showed the highest growth inhibition (lowest MICs) and fungicidal (lowest MFCs) activities compared to the other three peptides. Data is presented in Tables 1 and 2 below and represent the results of three independent experiments. Values are expressed in µg/mL.

TABLE 1

| Minimum inhibitory concentration (µg/mL) | | | | |
|---|---|---|---|---|
|  | BmKn2 | dBmKn2 | Kn2-7 | dKn2-7 |
| CA494 | >100 | >100 | 50-100 | 50-100 |
| CA526 | 50-100 | 50-100 | 50-100 | 12.5-25 |
| CA2519 | 50-100 | 25-50 | 25-50 | 12.5-25 |
| MYA 2876 | 25-50 | 50-100 | 25-50 | 6.25-12.5 |
| ATCC 64124 | 25-50 | 25-50 | 12.5-25 | 12.5-25 |

TABLE 2

| Minimum fungicidal concentration (µg/mL) | | | | |
|---|---|---|---|---|
|  | BmKn2 | dBmKn2 | Kn2-7 | dKn2-7 |
| CA494 | >100 | >100 | >100 | >100 |
| CA526 | 50-100 | 50-100 | 50-100 | 25-50 |
| CA2519 | 50-100 | 25-50 | 50-100 | 12.5-25 |
| MYA 2876 | 25-50 | 50-100 | 25-50 | 12.5-25 |
| ATCC 64124 | 25-50 | 25-50 | 25-50 | 12.5-25 |

Example 3: Time-Dependent Release of Calcein AM from MYA 2876 *C. Albicans* Cells Treated with dKn27 or Melittin Planktonic MYA 2876 cells were loaded with calcein AM fluorescent dye (ThermoFisher Scientific, Waltham, Mass., USA) for 2 hours, washed to remove free calcein AM, and then resuspended in fresh PBS. Cells were then treated with various concentrations of dKn2-7 or melittin (Sigma-Aldrich, St. Louis, Mo., USA), and calcein AM release from cells was monitored over 8 hours by fluorescence spectroscopy ($\lambda_{ex}$ 485 nm; $\lambda_{em}$ 530 nm) using a Tecan Spark 10M microplate reader (Tecan U.S., Morrisville, N.C.). Melittin is a known lytic peptide and was included as a positive control. Complete (100%) calcein AM release was determined by measuring the amount of calcein AM released from boiled cells. Cells treated with PBS alone were used as the vehicle control and are labeled as "Untreated Cells" in FIG. 1 and as "Control" in FIG. 9. A higher and more rapid release of calcein AM occurred at the lower concentration of dKn2-7, which is closer to the MIC (6.25-12.5 µg/mL), than at the higher concentration tested. Melittin showed a similar pattern. The results are provided in FIG. 1 and FIG. 9, which depict the same data graphed in two different ways. FIG. 1 depicts the results as raw fluorescence readings from the Tecan microplate reader in fluorescence units from the same experiment over a longer time period than FIG. 9, which depicts the results with emphasis on the first 4 hours and standardized to 100% release in boiled cells, i.e., as a percentage of total (100%) release from boiled cells. Thus, as depicted, 0% release is for cells treated with PBS alone (vehicle control). Data indicate that the peptides may have multiple mechanisms of fungal cell killing and the mechanism may be dependent upon the peptide concentration.

Example 4: Efficacy of dKn2-7 Against Planktonic *C. albicans* MYA 2876

Figure 2:
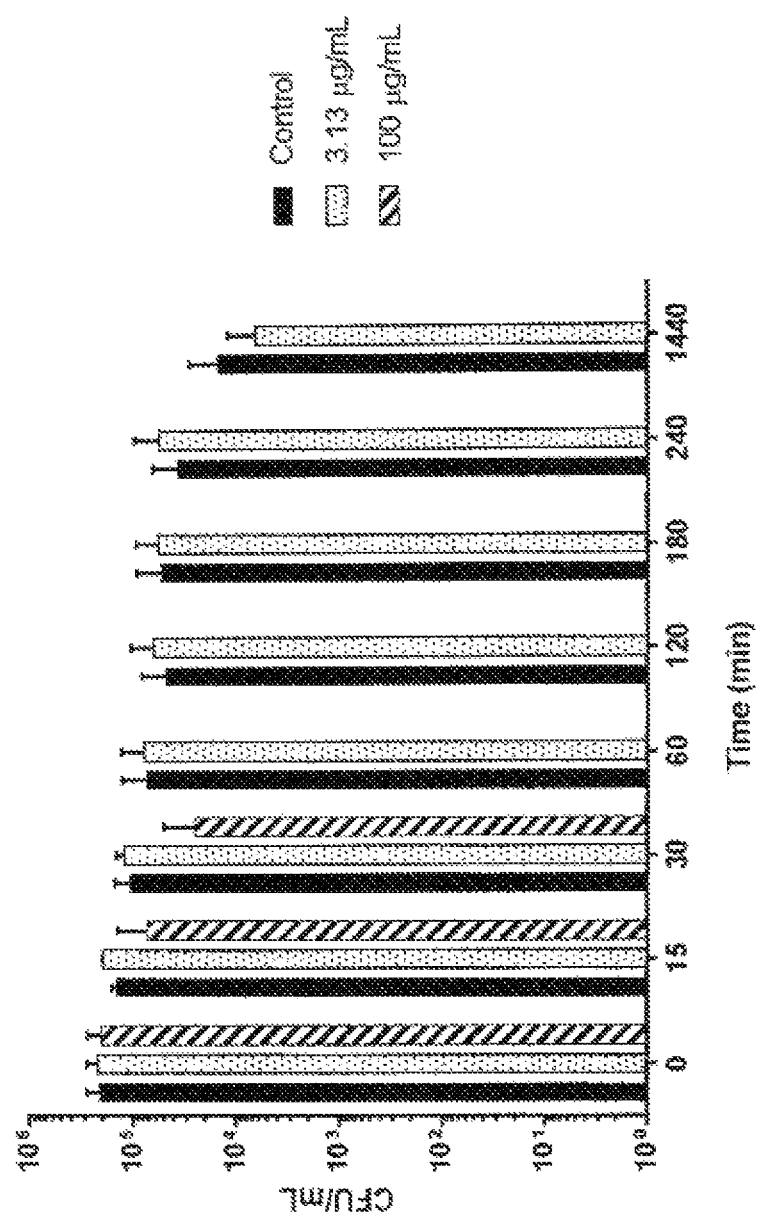
FIG. 2 depicts efficacy of dKn2-7 against planktonic C. albicans MYA 2876. Cells were treated with increasing concentrations of dKn2-7 in PBS for pre-determined durations of 0-24 hours and then tested for viability using colony forming unit (CFU) assays. Data represent the average of two independent experiments with triplicate samples for each treatment condition. Black bars represent control; stippled bars represent 3.13 µg/mL dKn2-7, and hatched bars represent 100 µg/mL dKn2-7.
Figure 3:
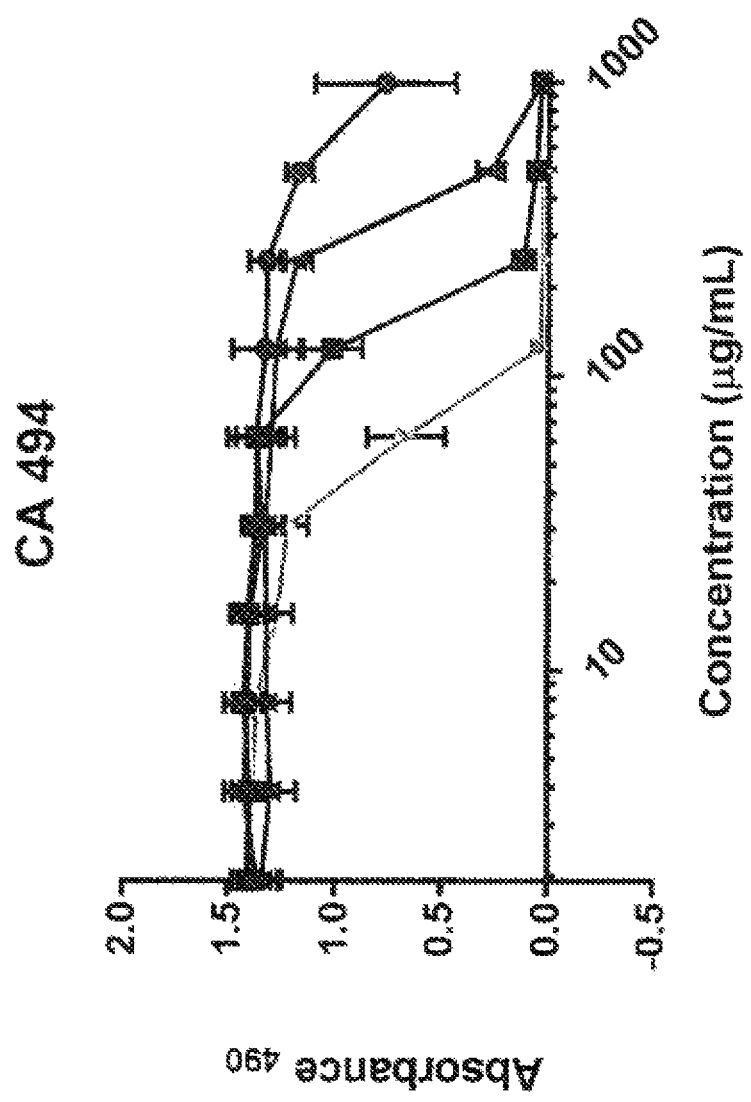
FIG. 3 depicts efficacy of BmKn2 (circles), dBmKn2 (squares), Kn2-7 (triangles), or dKn2-7 (inverted triangles) peptides against pre-formed C. albicans CA 494 biofilm following a 24-hour treatment with the antimicrobial peptides (AMPs). Biofilm viability was measured using the XTT assay with absorbance measured at 490 nm (Absorbance$_{490}$). Each data point represents the average of three experiments performed in triplicate.
Figure 4:
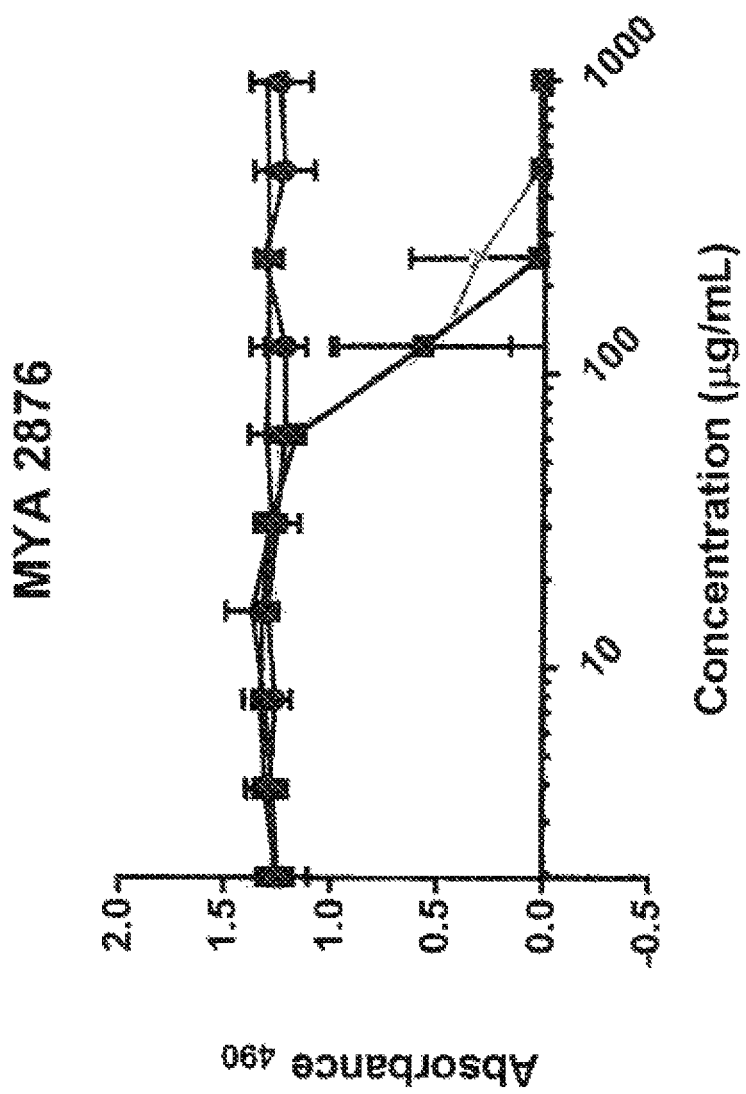
FIG. 4 depicts efficacy of BmKn2 (circles), dBmKn2 (squares), Kn2-7 (triangles), or dKn2-7 (inverted triangles) peptides against pre-formed C. albicans biofilm MYA2876 following a 24-hour treatment with the AMPs. Biofilm viability was measured using the XTT assay with absorbance measured at 490 nm (Absorbance$_{490}$). Each data point represents the average of three experiments performed in triplicate.
Figure 5:
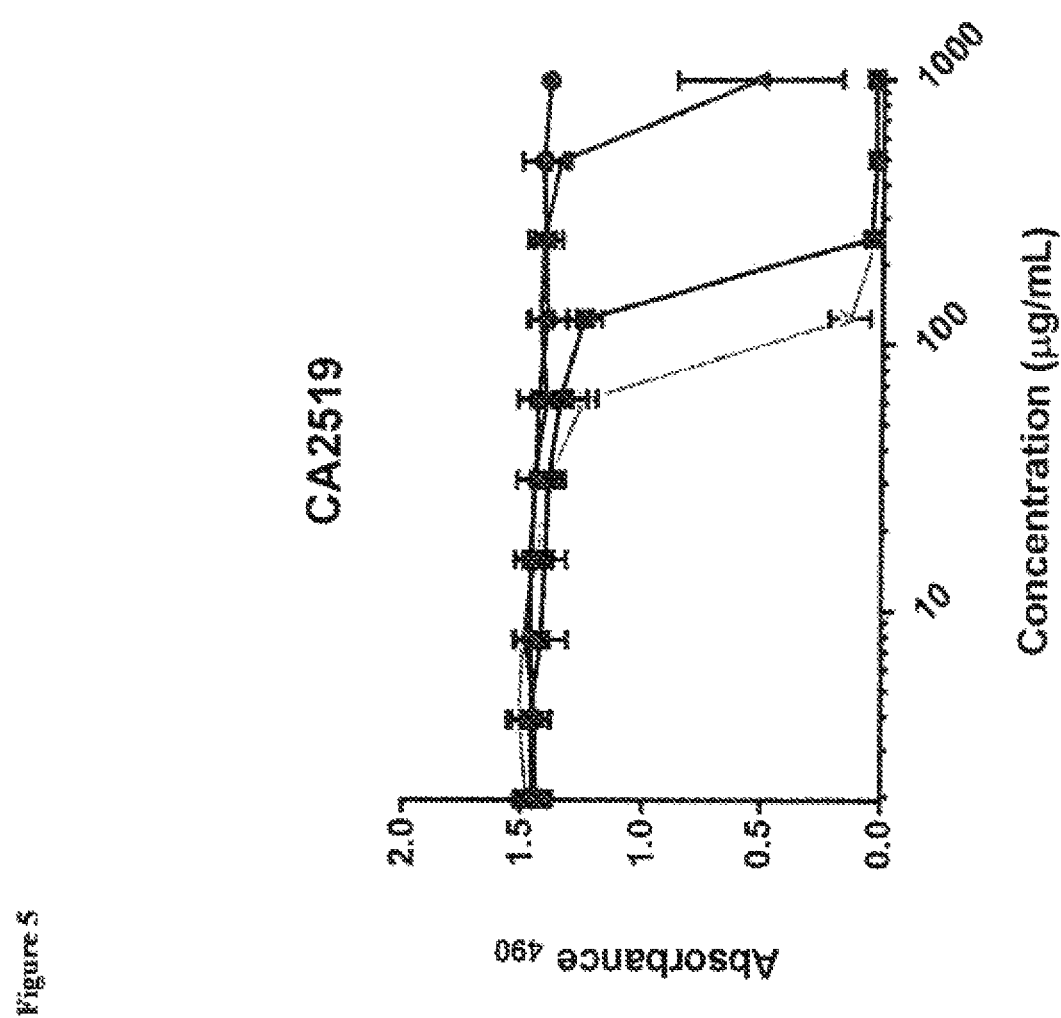
FIG. 5 depicts efficacy of BmKn2 (circles), dBmKn2 (squares), Kn2-7 (triangles), or dKn2-7 (inverted triangles) peptides against pre-formed C. albicans biofilm CA2519 following a 24-hour treatment with the AMPs. Biofilm viability was measured using the XT assay with absorbance measured at 490 nm (Absorbance$_{490}$). Each data point represents the average of three experiments performed in triplicate.
Figure 6:
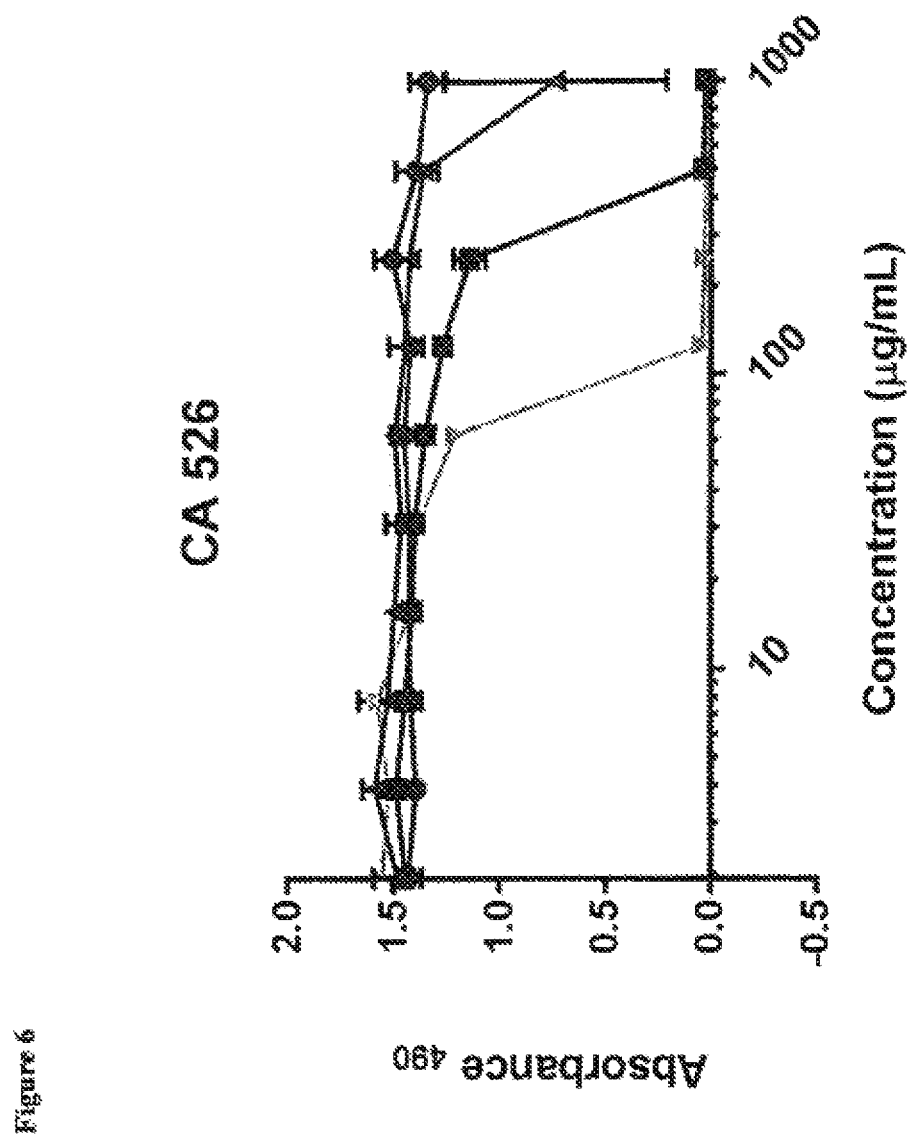
FIG. 6 depicts efficacy of BmKn2 (circles), dBmKn2 (squares), Kn2-7 (triangles), or dKn2-7 (inverted triangles) peptides against pre-formed C. albicans CA526 biofilm following a 24-h treatment with the AMPs. Biofilm viability was measured using the XTT assay with absorbance measured at 490 nm (Absorbance$_{490}$). Each data point represents the average of three experiments performed in triplicate.
Figure 7:
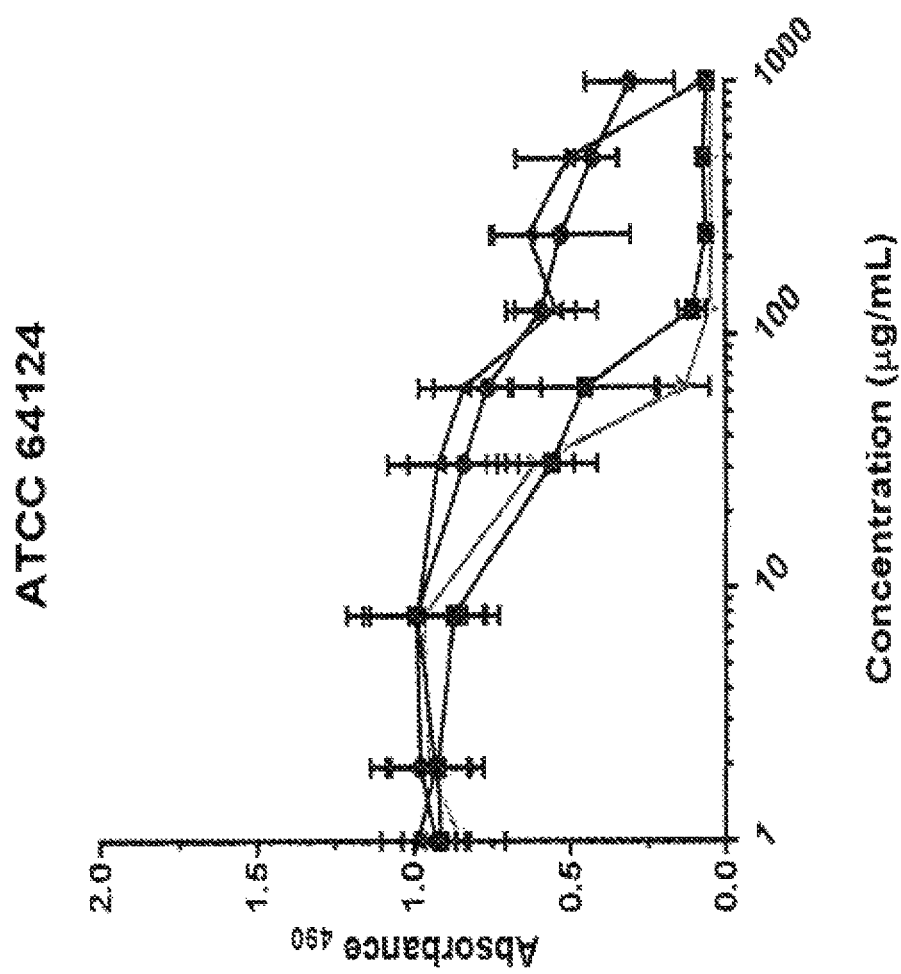
FIG. 7 depicts efficacy of BmKn2 (circles), dBmKn2 (squares), Kn2-7 (triangles), or dKn2-7 (inverted triangles) peptides against pre-formed C. albicans ATCC 64124 biofilm following a 24-hour treatment with the AMPs. Biofilm viability was measured using the XTT assay with absorbance measured at 490 nm (Absorbance$_{490}$). Each data point represents the average of three experiments performed in triplicate.

The killing efficacy of dKn2-7 against planktonic *C. albicans* MYA 2876 over time was assayed. Briefly, planktonic cultures of MYA 2876 were treated with dKn2-7 in PBS for various durations up to 24 hours, and CFU assays to test viability were performed after treatment using methodology based on the teachings provided in Karlsson, et al. ACS Chemical Biology, Vol. 4 No. 7, pages 567-579 (2009), the contents of which are incorporated by reference herein. Data is depicted in FIG. 2 and represent the average of two independent experiments with triplicate samples for each treatment condition. For samples treated with a concentration of 100 µg/mL dKn2-7, no CFUs were detected after 60 minutes of treatment. In contrast, the controls and samples treated with 3.13 µg/mL dKn2-7 remained relatively constant over 4 hours of treatment and showed a 1-log reduction in CFUs at the 24-hour time-point. These data reveal that the majority of the cell population is dead after treatment with 100 µg/mL of dKn2-7 for 60 minutes, even though complete release of calcein AM from cells was not observed (see FIG.

Figure 9:
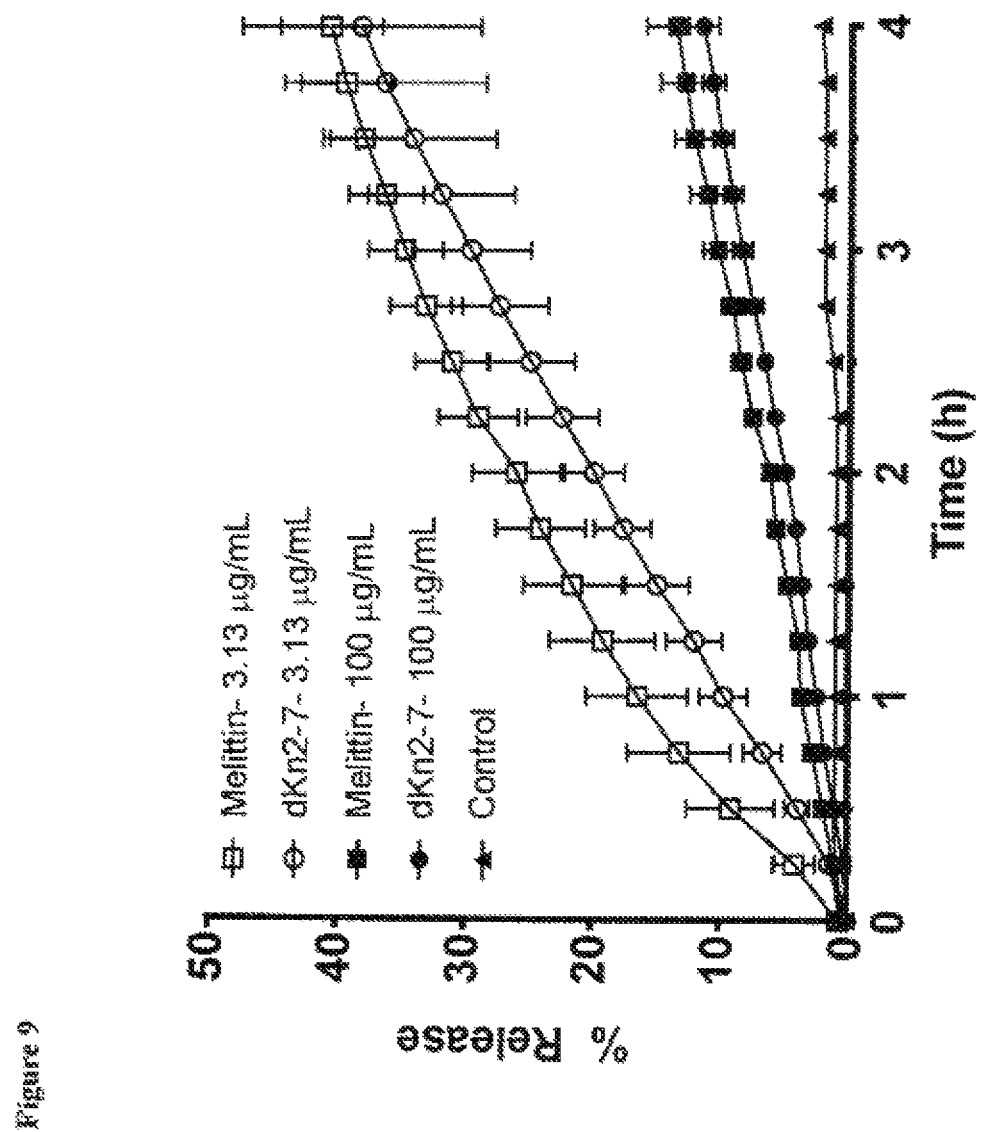
FIG. 9 depicts time-dependent calcein AM release (over 4 hours) from MYA 2876 C. albicans cells treated with 3.13 µg/mL dKn2-7 (open circles), 100 µg/mL dKn2-7 (shaded circles), 3.13 µg/mL melittin (open squares), or 100 µg/mL mellitin (shaded squares) and assayed to test for AMP-induced cell lysis. Planktonic MYA 2876 cells were loaded with calcein AM for 2 hours, washed to remove free calcein AM, and treated with various concentrations of dKn2-7 or melittin in PBS. Melittin, a known lytic peptide, was used as a positive control. Data are presented as percent of total (100%) calcein AM release, which was determined by measuring calcein AM release from boiled cells. Cells treated with PBS alone were used as the vehicle control, and data from these samples are labeled as "Control" in the figure (triangles). Calcein AM liberated from cells was quantified by fluorescence spectroscopy ($\lambda_{ex}$ 485 nm; $\lambda_{em}$ 530 nm). A greater release of calcein AM occurred after treatment with 3.13 µg/mL of dKn2-7 and melittin compared to treatment with 100 µg/mL. This result is opposite to the response pattern in FIG. 8, and thus suggests concentration-dependent mechanisms of action for dKn2-7 and melittin.

1 and FIG. 9). This finding suggests that dKn2-7 kills fungi via a mechanism that does not cause complete lysis of the cell membrane.

Figure 8:
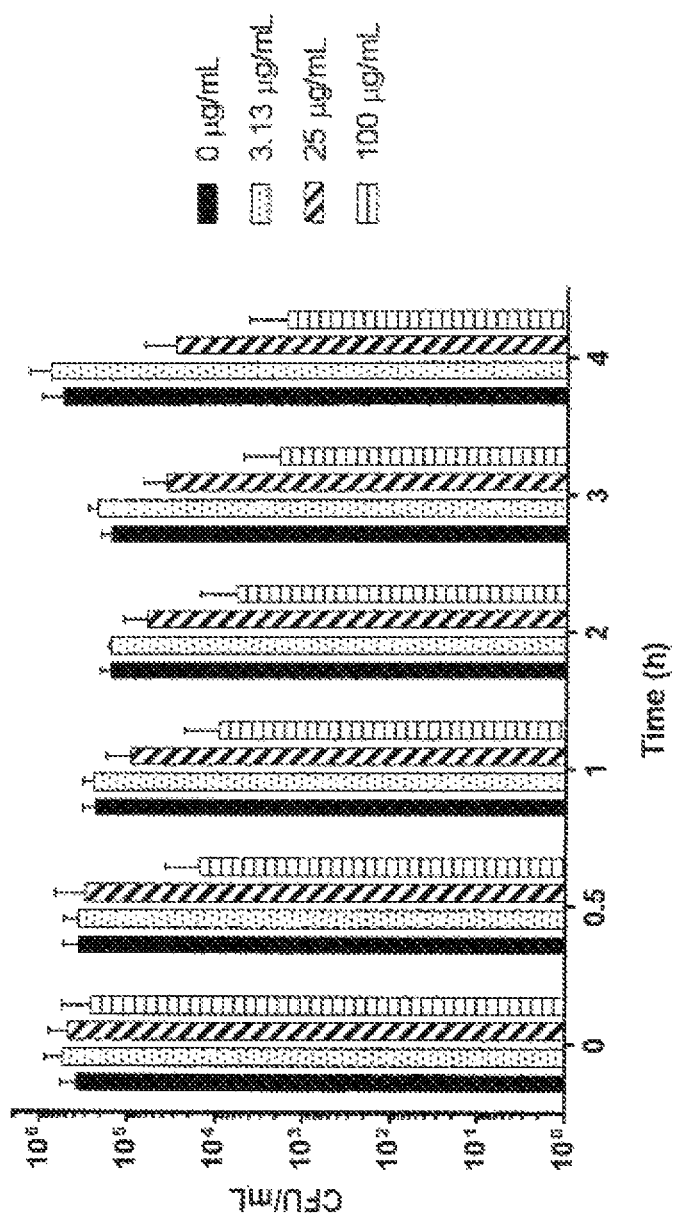
FIG. 8 depicts time-kill assay results which confirmed the fungicidal activity of dKn2-7 against planktonic C. albicans MYA 2876 cultures. Cells were treated with increasing concentrations of dKn2-7 in RPMI 1640 media for pre-determined durations of 0-4 hours and then tested for viability using CFU assays. Each data point represents the average of three experiments performed in triplicate. In the figure, 0 µg/mL dKn2-7 (black bars), 3.13 µg/mL dKn2-7 (stippled bars), 25 µg/mL dKn2-7 (hatched bars), and 100 µg/mL dKn2-7 (straight line bars) are depicted.

Because of a concern that the viability of cultures may have declined over time when PBS was used as the dosing solution vehicle, the time-kill experiment was repeated as described above, but using RPMI 1640 in place of the PBS as the dosing solution vehicle. Results of this experiment are depicted in FIG. 8, which includes data for 0 µg/mL, 3.13 µg/mL, 25 µg/mL, and 100 µg/mL dKn2-7. While a difference in results is evident when FIG. 2 and FIG. 8 are compared, data in FIG. 8 confirm the fungicidal activity of dKn2-7 against planktonic C. albicans MYA 2876 cultures.

Example 5: Efficacy of BmKn2, dBmKn2, Kn2-7 and dKn2-7 Peptides Against Pre-Formed C. albicans Biofilms The viability of various C. albicans biofilms (CA494, MYA 2876, CA 2519, CA 526 and ATCC 64124) in the presence of BmKn2, dBmKn2, Kn2-7 or dKn2-7 peptides was measured using the XTT assay (Sigma-Aldrich, St. Louis, Mo., USA) 24 hours after treatment. Results are depicted in FIGS. 3-7, and indicate that dBmKn2 and dKn2-7 caused 100% reduction in biofilm viability in all S fungal strains, and dKn2-7 showed up to a 4-fold higher efficacy against the fungal biofilms compared to the other three peptides. This indicates the D-amino acid forms of the peptides may be more stable against biofilm proteases. We note herein that the ATCC 64124 strain is ketoconazole resistant, and thus the data in FIG. 7 suggest that these peptides have activity against this drug resistant strain of C. albicans.

Example 6: Confocal Microscopy of MYA 2876 C. albicans Biofilms Treated with dKn2-7

Pre-formed biofilms of MYA 2876 C. albicans were treated with dKn2-7 (500 µg/mL) or vehicle only for 24 hours. The biofilms were subsequently washed and stained with fluorophores propidium iodide, SYTO 9, and Calcofluor White M2R (ThermoFisher Scientific, Waltham, Mass., USA), and confocal microscopy was performed.

Visualization of untreated biofilms showed a preponderance of SYTO 9 (green) staining with very little propidium iodide (red) staining, which indicates a high percentage of viable cells. In contrast, biofilms treated with 500 µg/mL dKn2-7 showed co-localization of SYTO 9 (green) and propidium iodide (red) fluorophores, resulting in a yellow/orange color distributed throughout the biofilm (data not shown). This is an indication of cell death, suggesting that treatment at this peptide concentration killed the pre-formed biofilm. These data compliment the XTT data in FIG. 3, indicating that the biofilm is metabolically inactive after treatment with 500 µg/mL of dKn2-7. This co-localization behavior was absent for the untreated biofilm (data not shown).

Example 7: Prophetic Example of a Field-Deployable Dosage Form

An easy-to-use, field-deployable dosage form could be made out of the antifungal peptides disclosed herein, e.g., dKn2-7, dispersed within electrospun nanofibers synthesized from a single naturally occurring or synthetic biocompatible polymer such as but not limited to: polylactic acid, polyethylene vinyl acetate, poly(lactic-co-glycolic acid), polyethylene glycol, poly(epsilon-caprolactone-co-ethyl ethylene phosphate), polycaprolactone, polylysine, polyvinyl alcohol, polyvinylpyrrolidone, collagen, cellulose acetate, gelatin, elastin, chitosan, fibrinogen, dextran, laminin, and hyaluronic acid, or a mixture of these polymers. The peptide and polymer could be synthesized and dissolved in an appropriate sterile solvent such as N, N-dimethylformamide, methanol, or other appropriate solvent. The peptide solution could be mixed with the polymer solution to form a homogeneous solution. The solution containing the peptide and polymer mixture could then be electrospun into a nanofibrous dressing. This could be accomplished by adding the mixture to a syringe pump for continuous flow of the peptide/polymer solution which contains an electrode. The other electrode can be connected to a collecting device such as but not limited to: metal screen, plate, and/or wheel. Different fiber packing densities could be obtained through manipulation of the collection stage; in the case of the wheel, rotations per minute could be altered to obtain desirable outcomes. Dispersal of the solution onto the collection stage could be achieved by altering the electric field that is applied; i.e. changing the voltages at the syringe pump and the collector. This electric field can be altered to affect the material that is obtained.

A solution of one or more antifungal peptides, or a mixture composed of one or more antifungal peptides combined with one or more additional pharmaceutically acceptable agents, e.g., antifungal, wound healing agent, or pain relieving agent, could be used along with the polymer to synthesize the electrospun dressing, resulting in a multifunctional wound dressing. Also, a coaxial electrospinning system could be used to obtain nanofibers that have an inner core composition that differs from the exterior. In this approach, an inner core polymer could be used to add mechanical strength and the outer core polymer could be used to enhance biocompatibility. This core-shell synthesis approach could also be used to design an outer shell for an immediate, burst delivery and the inner core for more sustained delivery of the therapeutic, or for sequential delivery of two or more different therapeutics. Alternatively, two or more separate syringe pumps containing different solutions could be used simultaneously to electrospin a material that is composed of two or more unique nanofibers. This approach could be used to incorporate two or more types of polymers or therapeutics into one dressing, if the individual components cannot be mixed into one solution due to an incompatibility, such as a requirement for different solvents.

Example 8: Hemolysis Assay

The hemolytic activity of BmKn2, dBmKn2, Kn2-7, dKn2-7, and melittin was assessed using human red blood cells (RBCs). The RBCs were prepared from human whole blood (BioreclamationIVT, Westbury, N.Y., USA) according to a previous report (Evans et al, J. Vis. Exp. (73), 50166, doi:10.3791/50166 (2013)). In brief, human whole blood was centrifuged, and the RBCs were washed with PBS 3-4 times and then diluted 1:20 of the original volume in PBS. Peptides at various concentrations from 0-400 µg/mL in PBS were mixed with an equal volume of the diluted RBCs in a 96-well microtiter plate and allowed to incubate for 1 hour at 37° C. The plate was then centrifuged at 500 g for 5 minutes and 100 µL of the supernatant was transferred to a 96-well, transparent, flat-bottomed plate. Sample absorbances were read at 490 nm using a BioTek Synergy HT plate reader (BioTek, Winooski, Vt.). PBS was used as a negative control (blank), and 1% Triton X-100 was used as a positive control for 100% hemolysis. The percent hemolysis for the unknown samples was calculated according to the following equation:

$$\% \text{ Hemolysis} = \frac{\text{Abs}_{490} - \text{Abs}_{490}^{PBS}}{\text{Abs}_{490}^{1\% \text{ Triton-X}} - \text{Abs}_{490}^{PBS}} \times 100\%.$$

Figure 10:
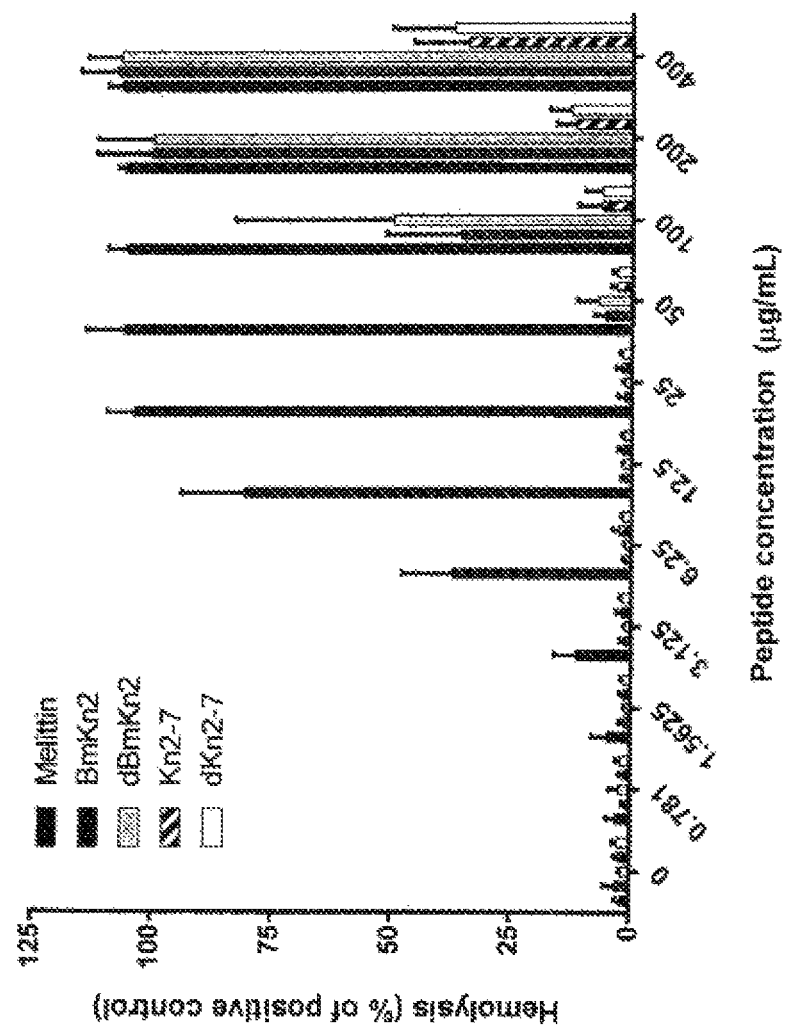
FIG. 10 depicts the hemolytic activity of BmKn2 (gray bars), dBmKn2 (outlined gray bars), Kn2-7 (hatched bars), and dKn2-7 (outlined open bars). Human red blood cells were incubated with the indicated peptides at various concentrations (µg/mL) for 1 hour at 37° C. Hemolysis was then determined by measuring the absorbance at 490 nm. Melittin (black bars) is a known lytic peptide and was included to confirm assay performance. All data were normalized to the amount of hemolysis induced by 0.1% Triton X-100, the positive control. Data indicate that Kn2-7 and dKn2-7 exhibited extremely low hemolytic activity compared to the other peptides tested.

Data presented in FIG. 10 depict 5 assays performed on different days using blood from different donors. Results indicate that hemolytic rates in untreated controls ranged from 2-3%. Melittin, a known cytolytic peptide, exhibited a significant increase in hemolysis compared to untreated controls at concentrations ≥3.125 µg/mL. BmKn2 and dBmKn2 started exhibiting a significant increase in hemolysis at 100 µg/mL. Kn2-7 and dKn2-7 started exhibiting an increase in hemolysis at 200 µg/mL, although these two peptides caused hemolytic rates of only 12-13% compared to hemolytic rates of ~100% observed for BmKn2, dBmKn2, and melittin at this dose. The concentration at which significant hemolysis was detected for Kn2-7 and dKn2-7, i.e., 200 µg/mL, is well above the range of minimum fungicidal concentrations (MFCs), i.e., 12.5-100 µg/mL, observed for these two peptides (see Table 2) against 6 of the 7 C. albicans strains. These results indicate that Kn2-7 and dKn2-7 should have a good safety profile and be less toxic than BmKn2 and dBmKn2 against red blood cells in vivo.

Example 9: Stability of Peptides in Human Serum

The stability of Kn2-7 and dKn2-7 (50 µg/mL) were studied in 25% human serum (v/v) (BioreclamationIVT, Westbury, N.Y., USA) in 1640 RPMI media (made with 165 mM MOPS, pH 7.0) or in 100% 1640 RPMI medium at 37° C. (H. Jenssen, S. I. Aspmo, Serum stability of peptides, Peptide-Based Drug Design (2008) 177-186.) At predetermined time points, 100 µL aliquots of each solution was removed and thoroughly mixed with 200 µL of 96% ethanol. This was incubated on ice for 15 minutes followed by centrifugation at 10,000 g for 5 minutes to pellet the precipitated proteins. The supernatant (200 µL) was carefully removed, spiked with peptide 1018 (VRLIVA-VRIWRR; SEQ ID NO. 3) at 1 µg/mL as the internal standard, and stored at −20° C. prior to liquid chromatography-mass spectrometry (LC/MS) analysis. Peptide 1018 is a synthetic peptide derived from bactenecin, a bovine neutrophil host defense peptide. (Mansour, S. C., et al. (2015) J. Pept. Sci., 21, 323-329. doi: 10.1002/psc.2708. The peptide sequence was synthesized by Genemed Synthesis Inc. (San Antonio, Tex.).

Liquid chromatography was performed on a Shimadzu HPLC system (Shimadzu Scientific Instruments, Inc., Columbia, Md.). A 10-µl aliquot of the sample was injected into an Agilent ZORBAX Eclipse XDB 80 Å C18 (2.1×50 mm, 5 µm) column (Agilent, Santa Clara, Calif.) held at 40° C. Mass spectrometric analysis was carried out on an AB Sciex API 4000 mass spectrometer (AB Sciex, Framingham, Mass.) with an electrospray ionization (ESI) interface and triple quadrupole mass analyzer. The peak areas of Kn2-7 and dKn2-7 on the LC-MS chromatograms were standardized to the peak area for peptide 1018.

Figure 11:
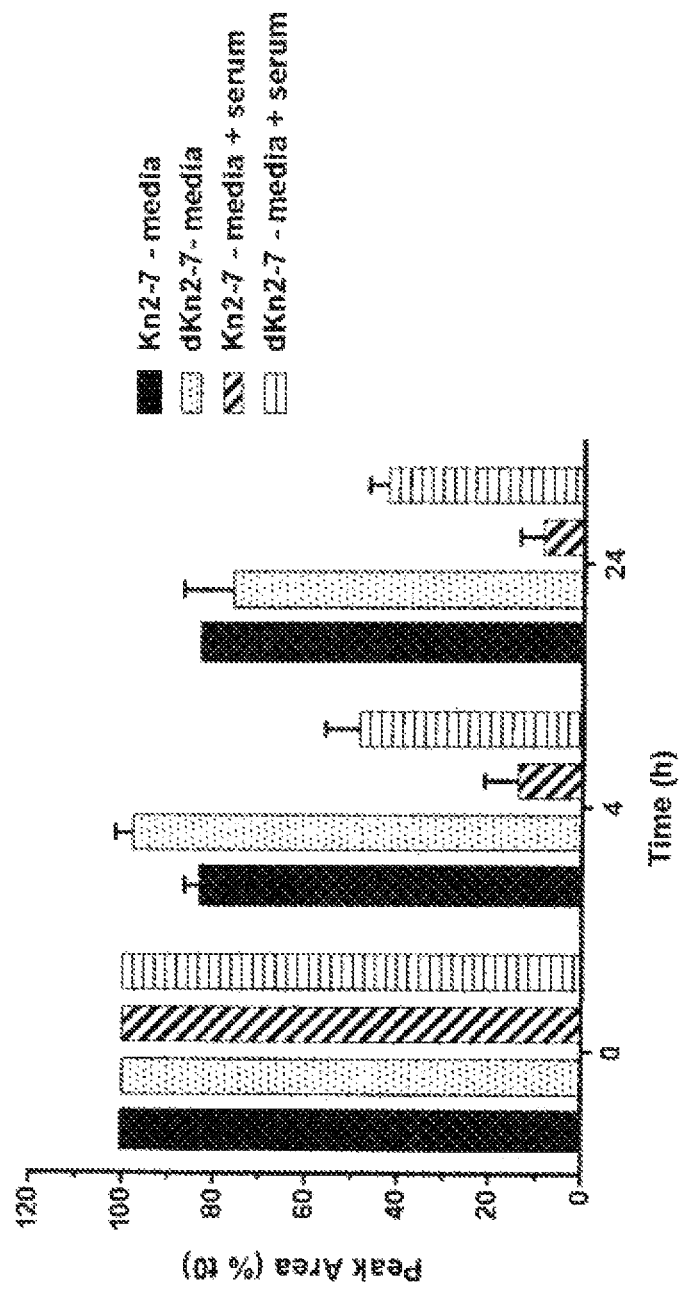
FIG. 11 depicts the stability of peptides in human serum. The stability of Kn2-7 and dKn2-7 in 25% (v/v) human serum in RPMI 1640 culture medium (hatched bars and straight line bars, respectively) and 100% RPMI 1640 culture medium (black bars and stippled bars, respectively) was evaluated over 24 hours using liquid chromatography-mass spectrometry (LC-MS). In 25% serum, dKn2-7 was present at significantly higher levels than Kn2-7 at both 4 and 24 hours, suggesting that the D-form is more stable against serum proteases.

Data are presented in FIG. 11 as a percent of the values at time=0 hour (t0), which were set to 100%, and represent the average and standard deviation of 3 individual experiments. Results indicate that the amounts of Kn2-7 and dKn2-7 in 100% culture medium were reduced by about 20% at 24 hours, with no clear difference between the L- and D-forms. In 25% serum, dKn2-7 was present at significantly higher levels than Kn2-7 at both 4 and 24 hours, suggesting that the D-form is more stable in the presence of serum than the L-form. About 43% of dKn2-7 and only about 9% of Kn2-7 remained in the samples after 24 hours in 25% serum. This indicates that using D-amino acids does stabilize the peptide against proteolytic degradation, and dKn2-7 should have greater stability than Kn2-7 against serum proteases in vivo.

Example 10: Antifungal Activity of Antimicrobial Peptide-Loaded Microfiber Wound Dressings In this particular experiment, we focused on developing a wound dressing capable of immediate and/or modified release of dKn2-7 to help combat fungal infections in wounds. As such, dKn2-7 was incorporated into microfibers composed of different polysaccharide blends. In vitro assays were used to determine the effect of fiber composition on the release profiles of the peptide over 24 hours as well as the antifungal efficacy of the dKn2-7 released from fibers against planktonic yeast.

Methods:
Wet-Spinning of Fibers:

An aqueous doping solution of each one of the following was homogenized, degassed, and 10 mL placed into a syringe: 2% sodium alginate (w/v), 2% sodium alginate/0.1% chitosan oligosaccharide lactate, or 2% sodium alginate/0.2% chitosan oligosaccharide lactate (all polymers were purchased from Sigma-Aldrich, St. Louis, Mo., USA). A 2-inch long 28G blunt tipped needle was attached to the syringe using a 90° connector before it was placed into a ChemGlass syringe pump (Neta Scientific, Hainesport, N.J., USA) located on an automated jack stand (ThorLabs, Newton, N.J., USA). The needle tip was lowered into a beaker containing 350 mL 1% (w/v) aqueous $CaCl_2$). A stainless steel collection cylinder (2-inch diameter) was also lowered into the beaker of $CaCl_2$ and attached to a VELP overhead stirrer (Thomas Scientific, Swedesboro, N.J., USA). The cylinder was rotated at 50 rpm and the syringe pump set to inject the alginate solution into the $CaCl_2$ at 10 mL/h with the jack stand set to oscillate the syringe pump up and down a distance of 30 mm at 0.25 mm/s. The resulting fibers created by this process were collected on the steel cylinder for the hour while the doping solution was extruded from the syringe and allowed to sit in the $CaCl_2$ solution for an additional 30 minutes afterward. Fibers were rinsed by spinning in deionized water for 1 minute. A razor blade was used to cut through the fibrous mat vertically so that the fibers could be removed from the collection cylinder. Fibers were placed in a 50 mL conical tube, frozen at −80° C., and then lyophilized overnight to obtain dry fibers.

Loading dKn2-7 into Fibers:

Dried fibers were cut into sections, weighed, and placed into a 12-well plate containing an aqueous dKn2-7 solution (200 µg/mL, 1 mL solution/10 mg fiber) and allowed to shake gently at room temperature for 2 hours. Additional fiber sections were treated the same, but soaked in water rather than dKn2-7 solution to act as non-peptide controls in future experiments. Fibers were removed from solution, frozen at −80° C., and then lyophilized overnight. Remaining dKn2-7 from the loading bath was collected to assess loading efficiency.

Loading Efficiency Assay:

dKn2-7 concentrations in the residual loading bath solutions were measured using Bio-Rad protein assay dye reagent according to the manufacturer's protocol. Loading efficiency was determined by the following equation:

$$\% \text{ Loading Efficiency} = \frac{200 - (\text{peptide concentration in residual loading bath})}{200} \times 100\%$$

Figure 12:
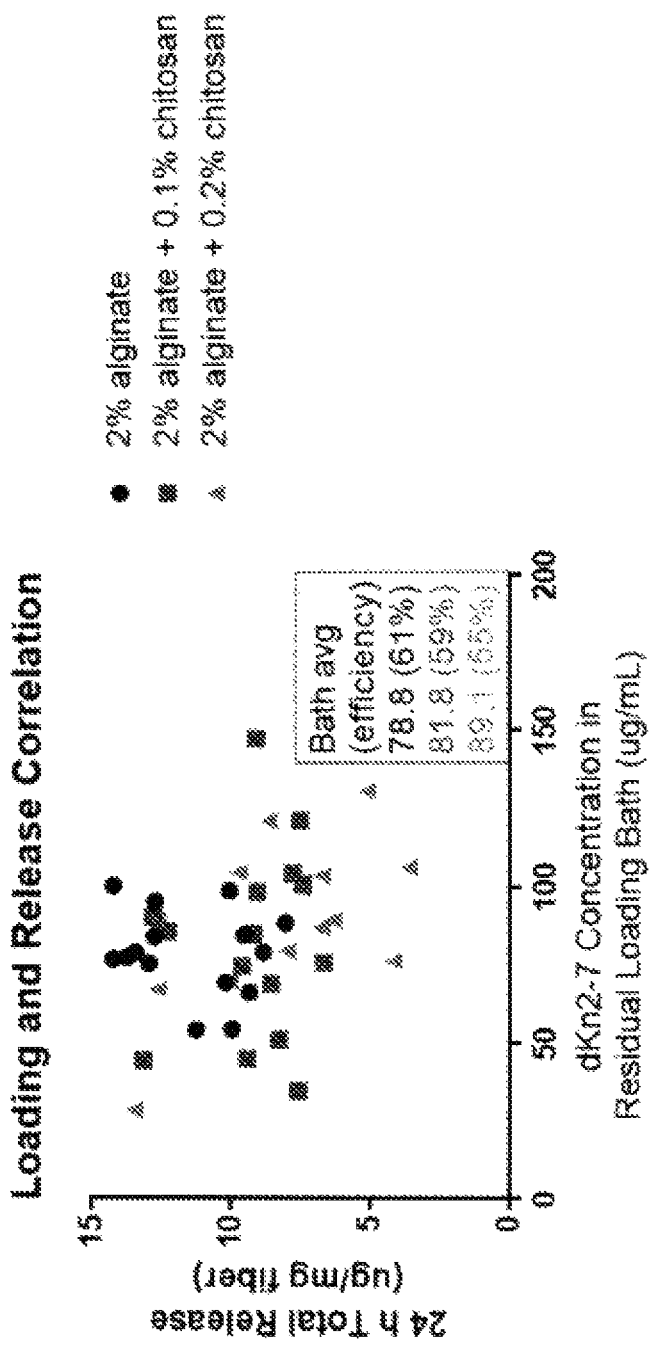
FIG. 12 depicts correlation between dKn2-7 loading efficiency (residual µg/mL dKn2-7 remaining in loading bath, x axis) and total dKn2-7 release (µg/mg fiber) over a 24 hour time period (y axis) for fiber types: 2% alginate (circles), 2% alginate+0.1% chitosan (squares) and 2% alginate+0.2% chitosan (triangles). Data show that increasing amounts of chitosan in the fibers lead to a decrease in average loading efficiency, although the differences among the three groups were not statistically significant due to the variability in loading from batch-to-batch within each group.

No statistical differences were seen between loading efficiency by fiber type or correlation between loading efficiency and 24-hour total release. See FIG. 12 dKn2-7 Release from Fibers:

Fibers (10-11 mg) were placed into 5 mL tubes with 2.5 mL phosphate buffered saline (PBS) and incubated at 37° C. with shaking at 100 rpm. At 0.25, 0.5, 1, 2, 4, 6, and 24 hours, the tubes were placed in a centrifuge and spun at 3500 rpm for 30 seconds to aggregate the fibers. A 1-mL aliquot was collected from the supernatant and a fresh 1-mL volume of PBS was added to the tube before placing it back in the incubator. dKn2-7 concentrations in these aliquots were determined using Bio-Rad protein assay dye reagent according to the manufacturer's protocol.

Figure 13:
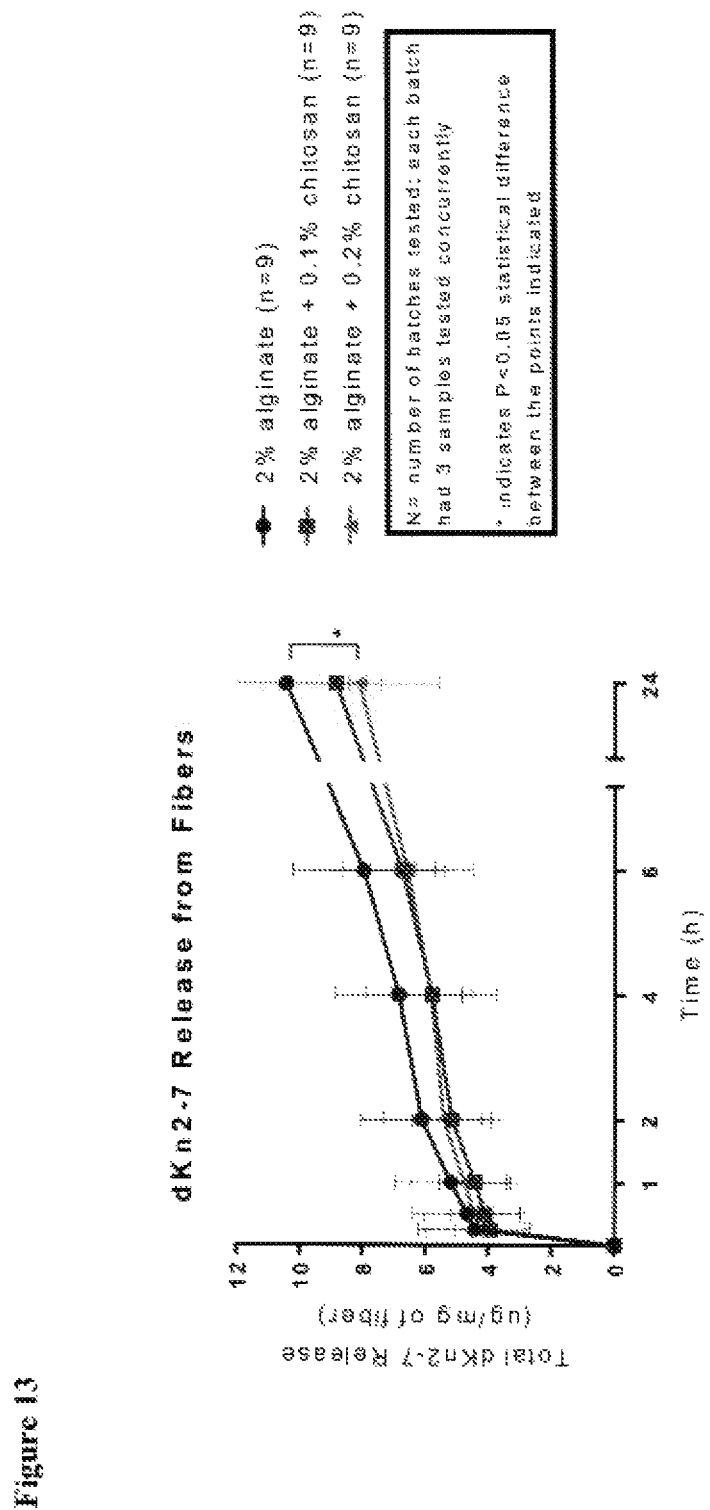
FIG. 13 depicts dKn2-7 release (μg/mg of fiber) from fiber types: 2% alginate (circles), 2% alginate+0.1% chitosan (squares) and 2% alginate+0.2% chitosan (triangles) over time. As depicted, N represents the number of batches tested, where each batch had 3 samples tested concurrently; * represents p<0.05 statistical difference between the points indicated. Data show that fiber composition does not have a significant effect on the amount of peptide released at the initial timepoint (the burst release), but does affect the subsequent rate of peptide released over longer periods of time with alginate/chitosan blends resulting in slower peptide release compared to alginate only fibers.

We have observed trends of decreasing total dKn2-7 release with increasing amounts of chitosan in the fibers. The only statistically different point is between the alginate only fibers and the high chitosan content fibers at 24 hours. Fibers appear to have similar burst releases with lower sustained release from the chitosan containing blends. See FIG. 13.

Ca2+ Release from Fibers:

Initial calcium release from the fibers was assessed and compared against Kaltostat® (ConvaTec, Bridgewater, N.J.) to assess the fibers' potential as a hemostatic dressing. Calcium concentrations in the 0.25-hour release samples collected during the dKn2-7 release studies were determined using a calcium colorimetric assay (Sigma-Aldrich, St. Louis, Mo., USA) according to the manufacturer's protocol. The Kaltostat® fibers were subjected to the same dKn2-7 loading procedures as our fibers.

Figure 14:
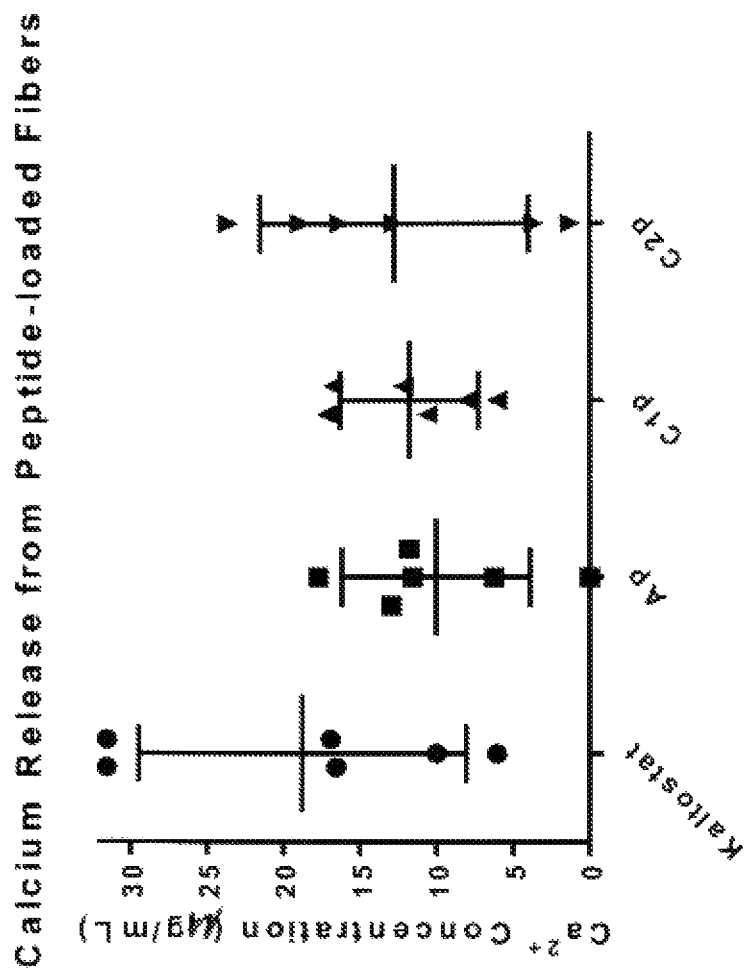
FIG. 14 depicts calcium release (μg/mL) from dKn2-7 peptide-loaded fiber types: 2% alginate with dKn2-7 (Ap); 2% alginate/0.1% chitosan with dKn2-7 (C1p); 2% alginate/0.2% chitosan with dKn2-7 (C2p) and Kaltostat® loaded with dKn2-7 (Kaltostat®). Data show no statistical differences in early (first 15 minutes) $Ca^{2+}$ release among the fiber types.

No statistical differences in early Ca2+ release were observed between our loaded fibers (Ap: 2% alginate with dKn2-7; C1p: 2% alginate/0.1% chitosan with dKn2-7; C2p: 2% alginate/0.2% chitosan with dKn2-7) and dKn2-7-loaded Kaltostat®. However, for fibers that had not undergone the loading process, a non-repeated study (n=1) showed that our fibers released more Ca2+ (205-257 μg/mL) than Kaltostat® (64 μg/mL). See FIG. 14.

Antifungal Activity of Fibers Against Planktonic *C. albicans*:

*C. albicans* MYA 2876 (100 μL at $10^5$ cells/mL of media) were added to the upper chamber of 24-well Transwell® plates (Corning, Corning, N.Y., USA). Ten mg of fibers (either loaded or unloaded) were added to the lower chamber along with 900 μL of media (Dulbecco's modified Eagle's medium). Plates were incubated at 37° C. and 100 rpm. After 24-hour incubation, cells and media from the upper chamber were collected, brought up to 1 mL with fresh media to control for volume differences, and serially diluted. Aliquots (20 μL) from each dilution were plated on Sabouraud dextrose agar (SDA) plates in triplicate. Agar plates were incubated overnight and colony forming units enumerated to determine fungal viability from each sample.

Figure 15:
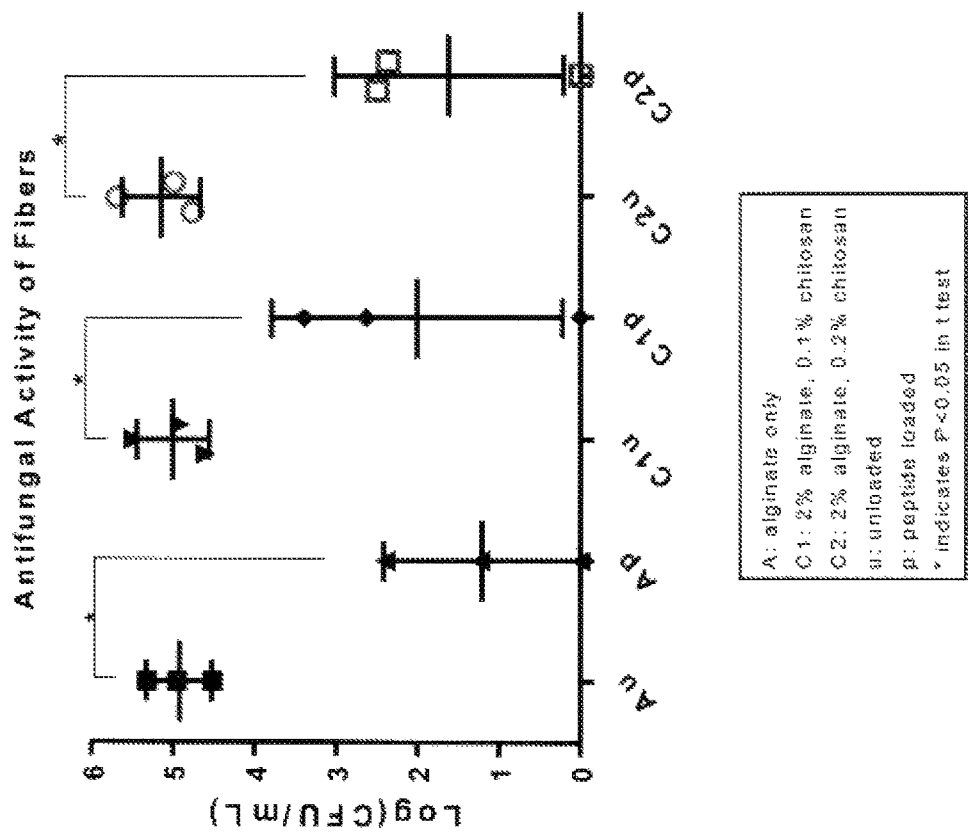
FIG. 15 depicts antifungal activity (provided as Log (CFU/mL)) of dKn2-7 loaded and unloaded fiber types: alginate only (A); 2% alginate+0.1% chitosan (C1) and 2% alginate+0.2% chitosan (C2). As depicted, "u" represents peptide unloaded fibers; "p" represents peptide loaded fibers; * represents p<0.05 in t test. Data show that peptide loaded fibers were able to reduce fungal viability by three or more orders of magnitude (comparable to ≥99.9% decrease in colony forming units) when compared to the same fibers without peptides.

Antifungal assays indicated high killing rates from 10 mg of fiber. Yeast viability for the loaded fibers was 0.081% for alginate fibers, 0.677% for 2% alginate/0.1% chitosan fibers, and 0.083% for 2% alginate/0.2% chitosan fibers when compared to the viability of their peptide-free fiber controls. FIG. 15 depicts these data in log (CFU/ml). As depicted, reductions in log (CFU/mL) are as follows (unloaded-loaded): alginate fibers, 3.72; 2% alginate/0.1% chitosan fibers, 3.00; 2% alginate/0.2% chitosan fibers, 3.54. These data show that peptide loaded fibers were able to reduce fungal viability by three or more orders of magnitude (comparable to ≥99.9% decrease in colony forming units) when compared to the same fibers without peptides.

Conclusions:

This experiment demonstrates that creating a wound dressing comprising an anti-fungal peptide of the instant invention is possible, and that such a dressing can not only provide an immediate release of the peptide, but also provide an extended, controlled release of peptide over time and produce an anti-fungal effect.

As illustrated above, dKn2-7 can be readily loaded into alginate-containing or alginate/chitosan-containing microfibers by allowing the fibers to soak in a dKn2-7-containing aqueous solution where the positively-charged peptide will be attracted to the negatively-charged alginate to adsorb via a reversible ionic bond. Once impregnated with dKn2-7, the alginate-containing or alginate/chitosan-containing fibers are capable of immediate release of the peptide, i.e., within 15 minutes, and controlled release of the peptide over at least 24 hours into an aqueous environment. By incorporating chitosan oligosaccharide lactate into the alginate fibers, the rate of dKn2-7 release can be modified; after the initial burst release of the peptide, fibers with chitosan released the peptide at a slower rate than alginate-only fibers.

What is claimed is:

1. A pharmaceutical composition comprising one or more peptides selected from the group consisting of Kn2-7, dKn2-7, BmKn2, and dBmKn2, wherein said BmKn2 and said Kn2-7 peptides comprise a combination of D form and L form amino acids; wherein said pharmaceutical composition further comprises one or more pharmaceutically acceptable carriers, excipients or diluents, and wherein said one or more peptides are present in an amount sufficient to treat a fungal infection in a subject in need thereof.

2. The pharmaceutical composition of claim 1, wherein said amount sufficient to treat a fungal infection in a subject in need thereof is from about 6 μmL to about 5 mg/mL.

3. The pharmaceutical composition of claim 1, further comprising one or more additional pharmaceutically acceptable agents.

4. The pharmaceutical composition of claim 3, wherein the one or more additional pharmaceutically acceptable agents is selected from the group consisting of an antimicrobial agent, an analgesic, a wound healing agent, a biofilm dispersal agent, and a biofilm inhibitor agent.

5. The pharmaceutical composition of claim 4, wherein the antimicrobial agent is selected from the group consisting of an antifungal agent, an antibacterial agent, and an antiviral agent.

6. The pharmaceutical composition of claim 1, wherein said pharmaceutical composition is a dosage form designed for topical administration.

7. The pharmaceutical composition of claim 6, wherein said dosage form designed for topical administration is a wound dressing.

8. The pharmaceutical composition of claim 7, wherein said wound dressing is a field-deployable wound dressing.

9. The pharmaceutical composition of claim 6, wherein said dosage form designed for topical administration comprises electrospun and/or wet-spun fibers.

10. The pharmaceutical composition of claim 9, wherein said wet-spun fibers comprise 2% alginate (w/v), 2% alginate/0.1% chitosan oligosaccharide lactate, or 2% alginate/0.2% chitosan oligosaccharide lactate.

11. A method of treating a polymicrobial infection and/or a fungal infection in a subject in need thereof comprising administering to the subject the pharmaceutical composition of any one of claims 1-10.

* * * * *